United States Patent
Prakash et al.

(10) Patent No.: US 8,998,609 B2
(45) Date of Patent: Apr. 7, 2015

(54) TECHNIQUES FOR STANDARDIZED IMAGING OF ORAL CAVITY

(71) Applicants: Manu Prakash, San Francisco, CA (US); Dhruv Boddupalli, Redwood City, CA (US); James Clements, E. Palo Alto, CA (US); Aditya Gande, Cupertino, CA (US)

(72) Inventors: Manu Prakash, San Francisco, CA (US); Dhruv Boddupalli, Redwood City, CA (US); James Clements, E. Palo Alto, CA (US); Aditya Gande, Cupertino, CA (US)

(73) Assignee: The Board of Trustees of the Leland Stanford Jr. University, Palo Alto, CA (US)

(*) Notice: Subject to any disclaimer, the term of this patent is extended or adjusted under 35 U.S.C. 154(b) by 0 days.

(21) Appl. No.: 13/764,764

(22) Filed: Feb. 11, 2013

(65) Prior Publication Data
US 2013/0209954 A1 Aug. 15, 2013

Related U.S. Application Data

(60) Provisional application No. 61/597,772, filed on Feb. 11, 2012.

(51) Int. Cl.
*A61C 5/14* (2006.01)
*A61B 1/24* (2006.01)
*A61B 1/04* (2006.01)
(Continued)

(52) U.S. Cl.
CPC ... *A61B 1/24* (2013.01); *A61B 1/04* (2013.01); *A61B 1/00165* (2013.01); *A61B 1/00011* (2013.01); *A61B 1/00045* (2013.01); *A61B 1/00009* (2013.01); *A61B 1/0646* (2013.01); *A61B 1/0002* (2013.01); *A61B 1/00188* (2013.01); *A61B 1/0005* (2013.01); *A61B 1/00108* (2013.01); *A61B 1/00147* (2013.01); *A61B 1/00172* (2013.01); *A61B 1/042* (2013.01); *A61B 1/043* (2013.01);
(Continued)

(58) Field of Classification Search
USPC ....................... 433/25, 29, 213, 214
See application file for complete search history.

(56) References Cited

U.S. PATENT DOCUMENTS 6,364,660 B1 * 4/2002 Durbin et al. .................... 433/29
6,386,867 B1 * 5/2002 Durbin et al. .................... 433/31
(Continued)

OTHER PUBLICATIONS

Brown, Matthew et al., "Automatic Panoramic Image Stitching using Invariant Features", "International Journal of Computer Vision", 2006, pp. 59-73, vol. 74, No. 1, Publisher: Springer, Published in: http://www.springerlink.com/index/10.1007/s11263-006-0002-3.
(Continued)

*Primary Examiner* — Ralph Lewis
(74) *Attorney, Agent, or Firm* — Evans Molinelli PLLC; Eugene J. Molinelli

(57) ABSTRACT

A method, system and apparatus for imaging an oral cavity of a subject include a bracket comprising a mouthpiece and a camera mount. The mouthpiece has upper and lower bite guides disposed on a posterior side and separated by an opening through the mouthpiece. The bite guides are spaced apart so a subject biting on the guides opens the oral cavity to inspection through the opening. The mount is disposed on an anterior side of the mouthpiece; and has a flange to engage and slide along the opening and an optical path for light to pass through the mount and mouthpiece. A clip on an anterior side of the mount is configured to removeably hold a camera to record light passing through the optical path from the posterior side of the mount. In one embodiment, the camera is a programmable cell phone with digital camera.

21 Claims, 23 Drawing Sheets

(51) Int. Cl.
*A61B 1/00* (2006.01)
*A61B 1/06* (2006.01)

(52) U.S. Cl.
CPC ............... *A61B 1/0684* (2013.01); *A61C 5/14* (2013.01); *A61B 1/00032* (2013.01); *A61B 1/00052* (2013.01)

(56) References Cited

U.S. PATENT DOCUMENTS

| | | | |
|---|---|---|---|
| 6,592,371 B2 * | 7/2003 | Durbin et al. | 433/214 |
| 6,821,116 B2 * | 11/2004 | Severance | 433/29 |
| 6,964,567 B2 * | 11/2005 | Kerschbaumer et al. | 433/26 |
| 7,596,253 B2 * | 9/2009 | Wong et al. | 382/128 |
| 7,826,728 B2 * | 11/2010 | Konno et al. | 396/16 |
| 2003/0148243 A1 | 8/2003 | Kerschbaumer et al. | |

OTHER PUBLICATIONS

Saxena, Ashutosh et al., "Learning Depth from Single Monocular Images", "Neural Information Processing Systems", 2005, p. 18, vol. 18, Publisher: The Neural Information Processing Systems Foundation, Published in: http://www.cs.cornell.edu/~asaxena/learningdepth/.

Saxena, Ashutosh, et al., "Make3D: Learning 3D Scene Structure from a Single Still Image", "IEEE Transactions on Pattern Analysis and Machine Intelligence", 2007, pp. 824-840, vol. 31, No. 5, Publisher: IEEE, Published in: http://www.ncbi.nlm.nih.gov/pubmed/19299858.

\* cited by examiner (PRIOR ART)

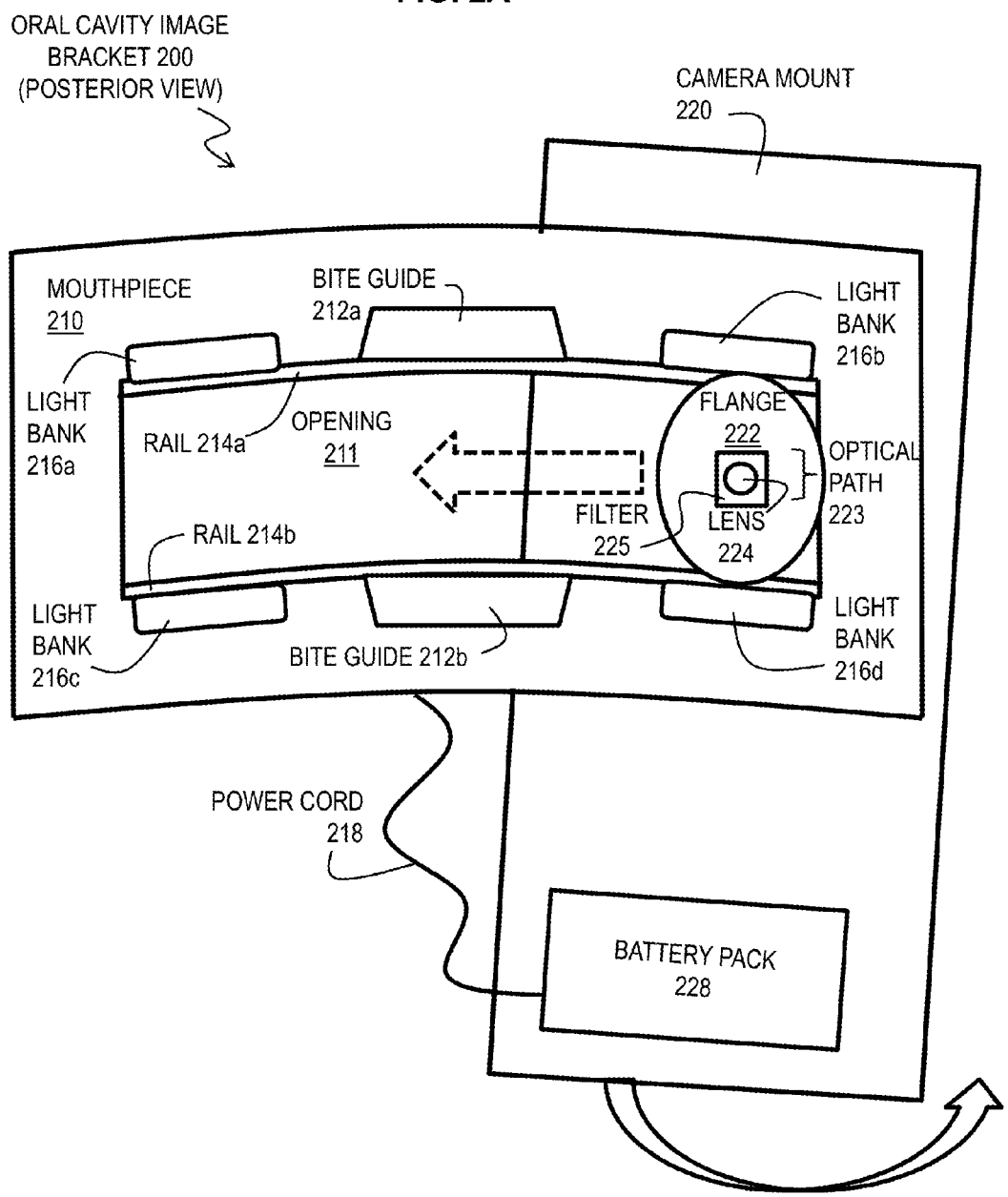

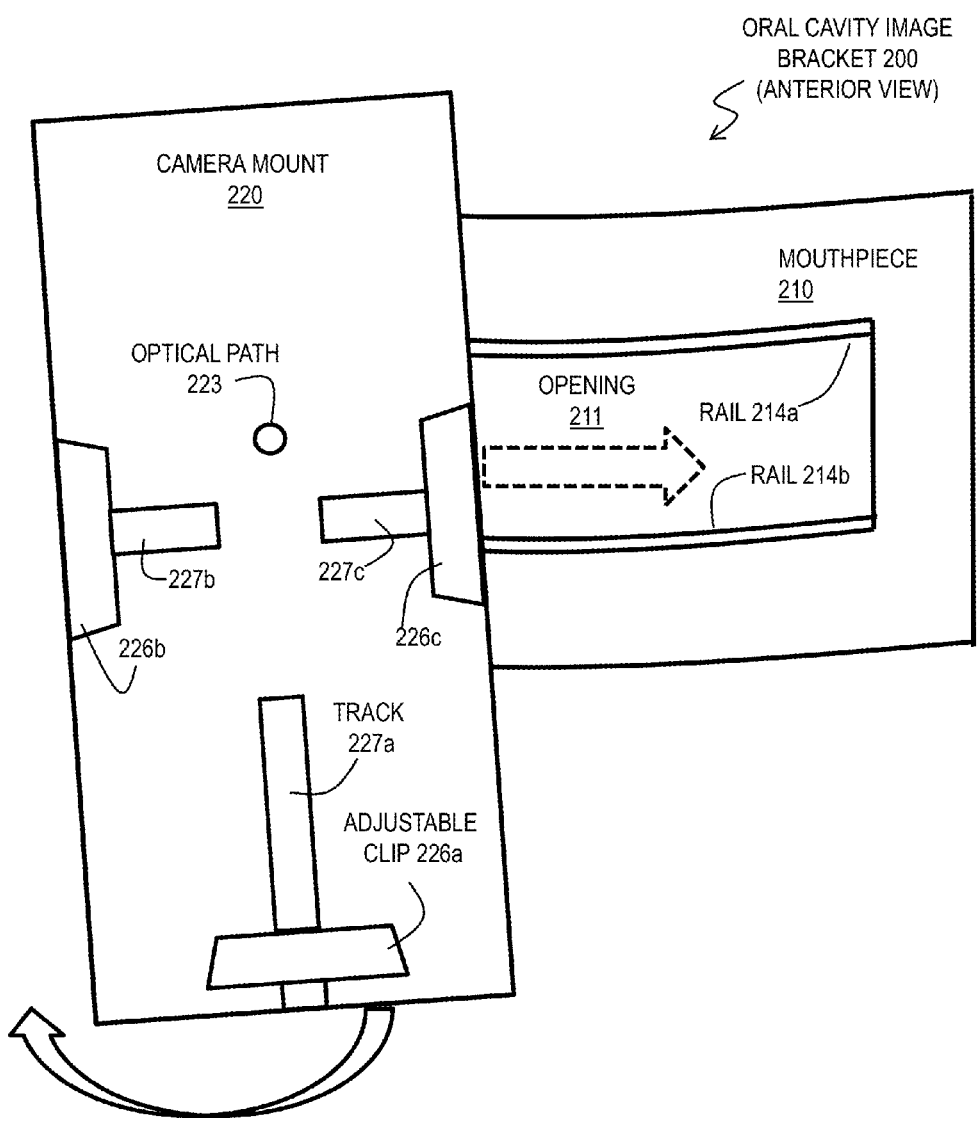

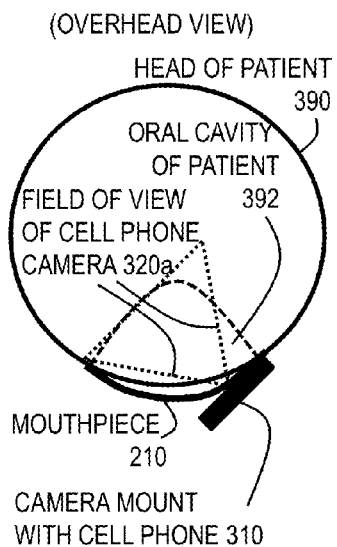
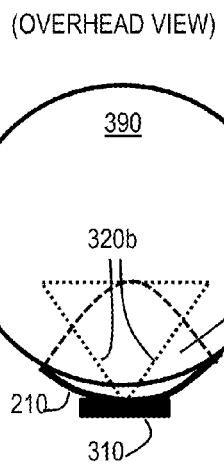
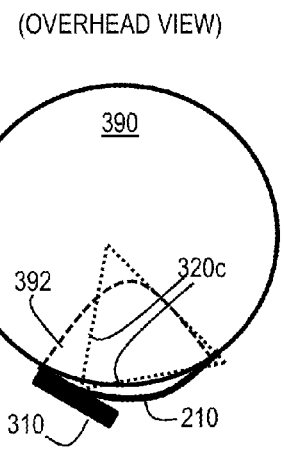
FIG. 3A (OVERHEAD VIEW)
FIG. 3B (OVERHEAD VIEW)
FIG. 3C (OVERHEAD VIEW)
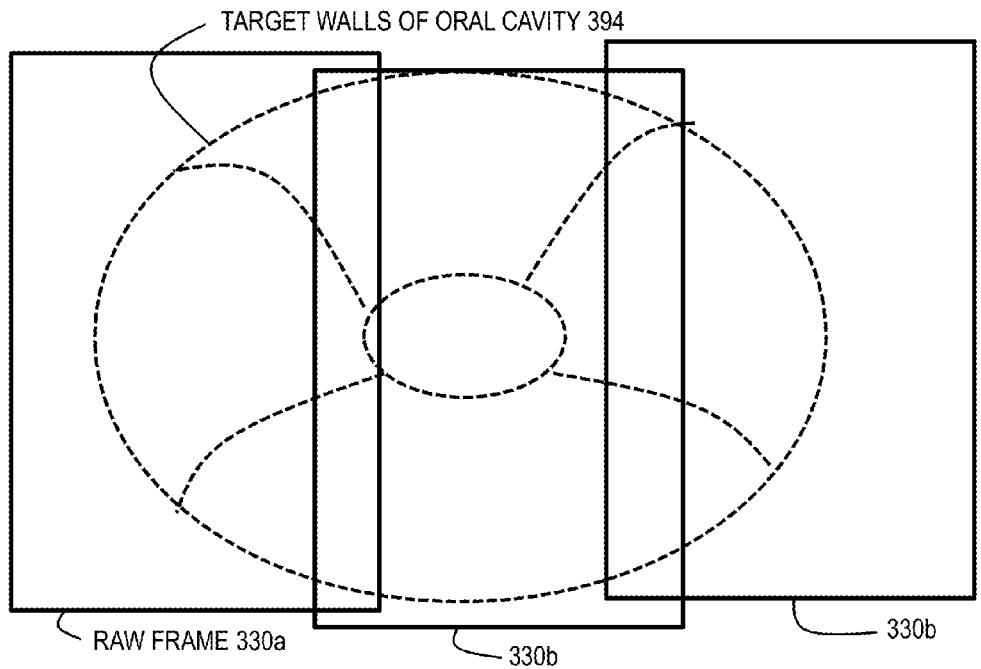
FIG. 3D

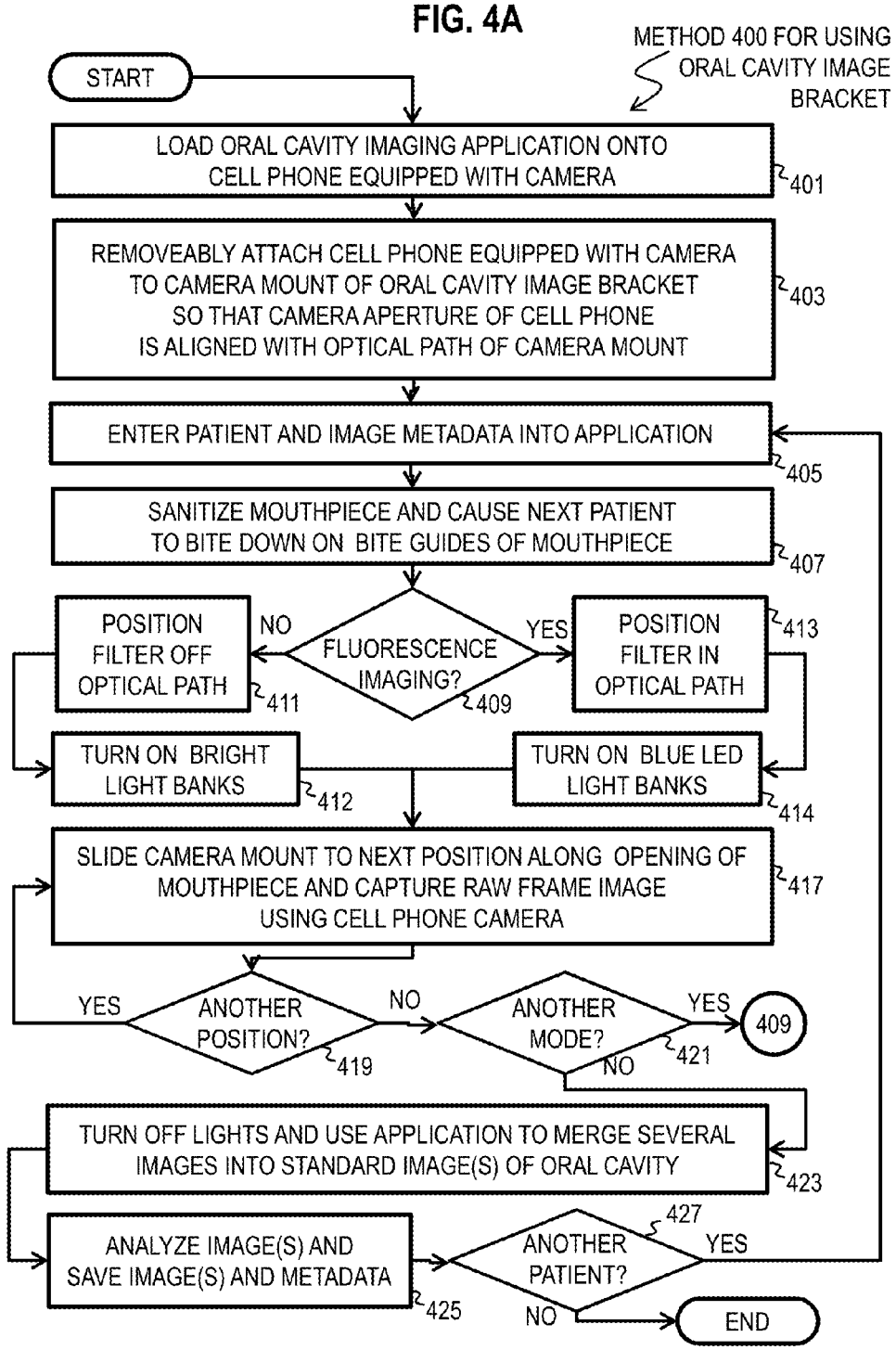

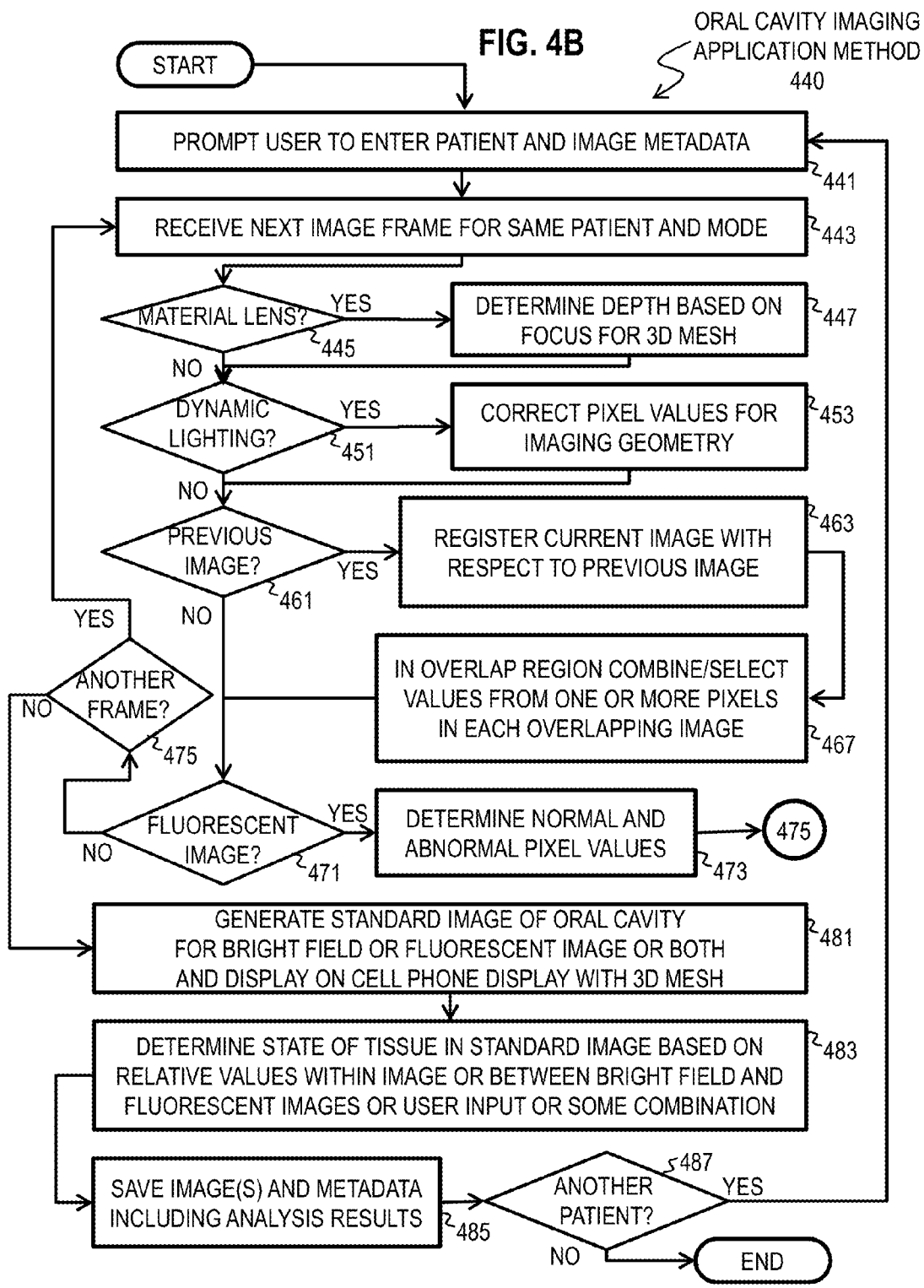

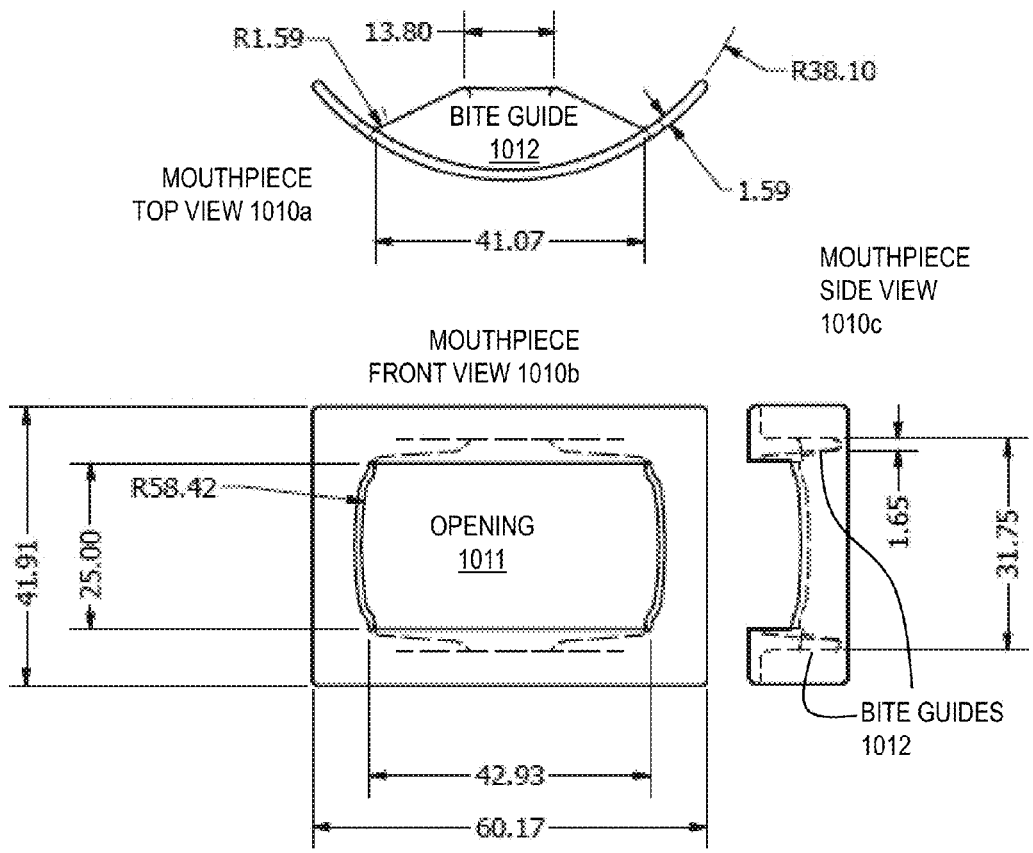
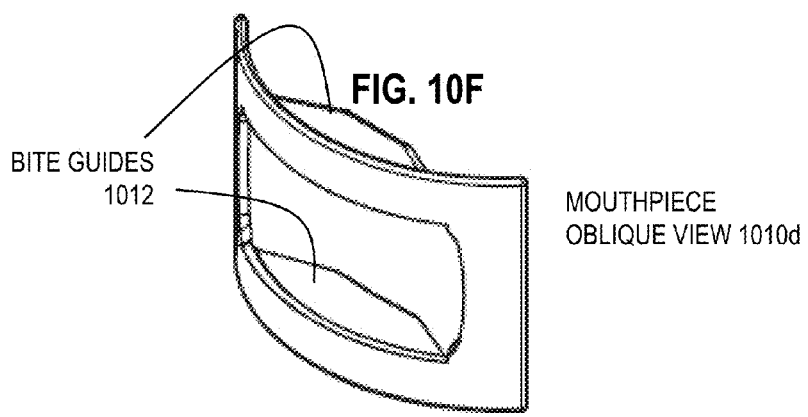

TECHNIQUES FOR STANDARDIZED IMAGING OF ORAL CAVITY

CROSS-REFERENCE TO RELATED APPLICATIONS

This application claims benefit of Provisional Appln. 61/597,772, filed Feb. 11, 2012, the entire contents of which are hereby incorporated by reference as if fully set forth herein, under 35 U.S.C. §119(e).

BACKGROUND OF THE INVENTION

The oral cavity in humans is an indicator of a number of diseases, including submucus fibrosis, gingivitis, oral cancer and others. For example, 400,000 cases of oral cancer are reported world-wide, one third of which are reported in developing countries with less than one doctor for every 50,000 patients. Tobacco chewing and smoking is the primary driver for the same where 70% of world tobacco consumption is in developing countries. Late discovery of an oral cancer has survival rates of 50% while early stage detection can improve the rate to more than 90%.

SUMMARY OF THE INVENTION

Even though the oral cavity is widely accessible for examination, no standards exist for comprehensive imaging of the cavity. Techniques are provided for some combination of inexpensive, efficient, comprehensive or standardized imaging of the oral cavity.

In a first set of embodiments, an oral cavity image bracket includes a mouthpiece and a camera mount. The mouthpiece of rigid material includes an upper bite guide and a lower bite guide, both disposed on a posterior side of the mouthpiece and separated by an opening through the mouthpiece. The upper bite guide and lower bite guide are spaced apart such that a subject biting down on the upper bite guide with the subject's upper jaw and biting up on the lower bite guide with the subject's lower jaw opens the subject's oral cavity to inspection through the opening. The camera mount is disposed on an anterior side of the mouthpiece and includes a flange configured to engage and slide along the opening of the mouthpiece. The camera mount further comprises an optical path and a clip. The optical path is configured for light to pass through the camera mount and through the opening in the mouthpiece. The clip is disposed on an anterior side of the camera mount, and is configured to removeably hold a camera on the anterior side of the camera mount to record light passing through the optical path from the posterior side of the camera mount.

In some embodiments of the first set, the camera is a cell phone with built in camera and on board processor.

In some embodiments of the first set, the mouthpiece further comprises a light source disposed on the posterior side of the mouthpiece and configured to illuminate the oral cavity of the subject.

In some embodiments of the first set, the optical path comprises a removeable optical filter that blocks light from a light source and passes fluorescent light emitted by tissue in the oral cavity of the subject in response to the light source.

In a second set of embodiments, an oral cavity imaging system includes the oral cavity image bracket described above plus a camera and a processor. The camera is removeably attached to the anterior side of the camera mount, and is configured to record and display an image based on light passing through the optical path from the posterior side of the camera mount. The processor is configured to merge data from a plurality of images recorded by the camera at a corresponding plurality of positions of the camera mount as the camera mount slides along the opening in the mouthpiece. In some embodiments of this set, the camera is a cell phone with built in digital camera and the processor on board the cell phone.

In a third set of embodiments, a method includes removeably attaching a camera to a camera mount of the oral cavity image bracket comprising the camera mount and a mouthpiece described above. The method also includes causing a subject to bite against the bite guides of the mouthpiece. The method further includes sliding the camera mount to a plurality of positions along the opening in the mouthpiece and causing the camera to capture a plurality of images corresponding to the plurality of positions. In some embodiments of this set, the method further comprises using a processor to merge data from the plurality of images into a standard image.

In a fourth set of embodiments, a computer program method includes determining distance from an imaging plane to a surface of an oral cavity of a subject based on relative intensity of a pixel in an image frame captured at the imaging plane compared to adjacent pixels in the image frame and a model of focusing optics. This is performed for each of multiple image frames of the oral cavity corresponding to multiple different look directions. The method includes merging, into a single image, pixels from the multiple image frames of the oral cavity.

In other sets of embodiments, an apparatus or computer readable medium is configured to cause the apparatus to perform one or more steps of the computer program method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A, FIG. 2B and FIG. 2C are block diagrams that illustrate an example oral cavity image bracket and system, according to an embodiment;

FIG. 3A, FIG. 3B and FIG. 3C are block diagrams that illustrate example fields of view from multiple positions of a camera mount along an opening in a mouthpiece of the example oral cavity image bracket, according to an embodiment;

FIG. 3D is a block diagram that illustrates example overlapping image frames captured from the multiple positions of the camera mount, according to an embodiment;

FIG. 4A is a flow chart that illustrates an example method for producing and using one or more standard images of the oral cavity utilizing the oral cavity image bracket and a cell phone with built in camera and processor, according to an embodiment;

FIG. 4B is a flow chart that illustrates an example computer program method for producing a standard image of the oral cavity based on overlapping image frames captured from the multiple positions of the camera mount, according to an embodiment;

FIG. 10A through FIG. 10F are scaled drawings for a mouthpiece and camera mount, according to a particular embodiment;

DETAILED DESCRIPTION

A method and apparatus are described for standardized imaging of the oral cavity. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of using a smart phone, e.g., a programmable cell phone with on board (built-in) processor and digital camera. However, the invention is not limited to this context. In other embodiments, other cameras are used, digital or otherwise, with or without on board processors. For example, in embodiments using a digital camera without a programmable on board processor, a separate programmable processor is provided on the mouthpiece or camera mount, and digital output from the camera is fed into the separate processor.

1. Overview

In many countries of the world, there is a lack of adequate dental screening and care. For example, in India, the Primary Health Centre (PHC) is the first point of contact for the community to get health care service and has no set criteria for employment of dentists in the rural areas of the country, leading to random appointments across the country. This has resulted in a huge shortfall in the oral care services at the primary level with private services being very cost-intensive.

Though a person's oral cavity is easily accessible via a regular inspection, it has been a challenge for clinicians and health-workers alike to assess the state of oral health of an individual in resource poor settings. The reasons for the same include complete lack of trained health workers who can assess oral hygiene problems purely by an inspection. Even in hospital settings at field sites without expensive equipment, it is difficult for clinicians to distinguish subtle neoplastic changes in oral mucosa from other inflammatory diseases.

Figure 1:
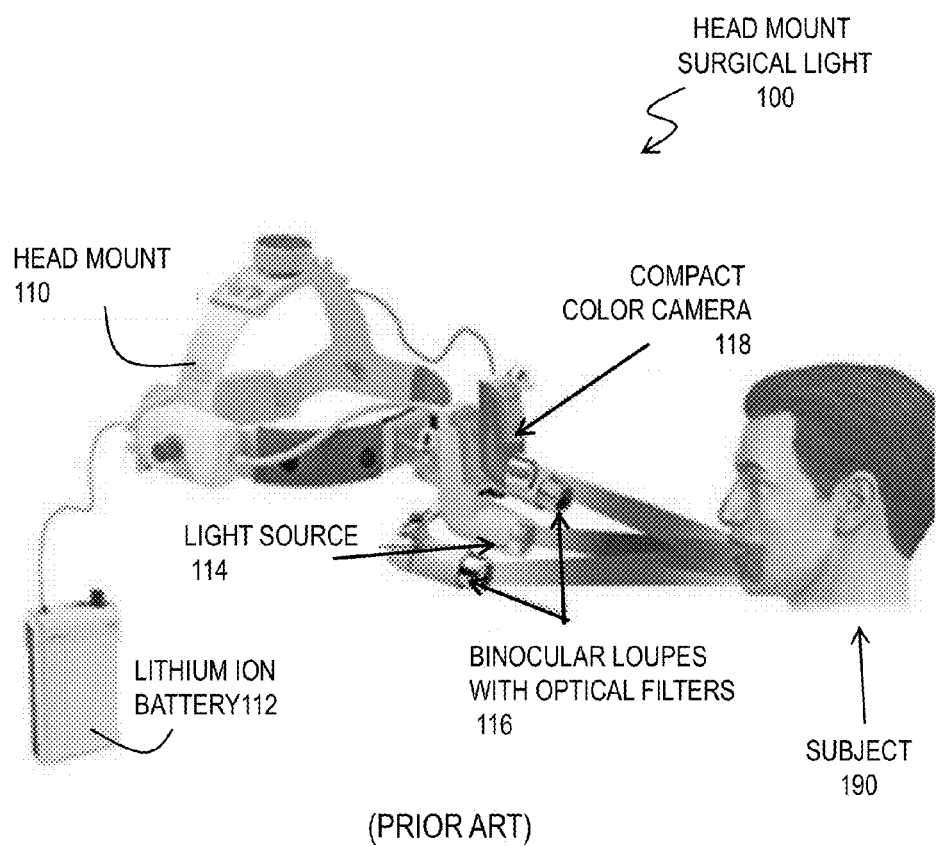
FIG. 1 is a block diagram that illustrates an expensive apparatus for imaging the oral cavity, as in the prior art.

FIG. 1 is a block diagram that illustrates an expensive apparatus for imaging the oral cavity, as in the prior art. The expensive apparatus is a head mount surgical light 100 that is placed on the head of a clinician in order to inspect and photograph the oral cavity of a subject 190, such as a patient. Mounted to the front of the head mount 110 is a light source 114 that illuminates the oral cavity when the mouth of the subject 190 is opened. The light emitted in two directions is captured in the two receptors of the binocular loupes 116 with optical filters. The two images are collected by the compact color camera 118, which is often a digital camera. Power for the light source 114 and camera 118 is provided by a lithium ion battery 112 worn by the clinician in a pocket of clothing or attached to a belt or other harness. For fluorescence imaging useful for some diagnoses, the optical filters of the binocular loupes 116 pass light in the fluorescence emission wavelength and block light in the other wavelengths of the illuminating light source 114. Such delicate and expensive equipment as head mount surgical light 100, including a trained operator, is in rare supply and often completely lacking in the rural areas of many countries.

The complete lack of screening and diagnostics tools for oral cancer in developing countries, where two-third of the world's cases of oral cancer exist and 70% of world consumption of tobacco occurs, clearly marks a very large gap in the current infrastructure (commercial and social) for tackling oral cancer worldwide.

Current methodology to document lesions found in oral cancer patients are based on manual sketches and are insufficient for conveying quantitative information to either the clinician or the patient. Such sketches used to document the progress of a lesion must be relied upon by radiotherapists to determine if a therapy is successful on many rural patients. A standardized oral cavity scanner would allow for a quantitative method for clinicians to track the progress of the lesions in individual patients before and during therapy.

Inventors have identified several needs that arise from discussions with current practicing field oncologists, oral and neck surgeons and cancer screening programs. These needs include the critical need for an ultra-wide angle imaging of the oral cavity, and image standardization for comparative analysis between different scans of the same patient and among different patients. The wide angle and standard images allow clinicians to assess the damage, and assess recovery during treatment. Furthermore, integration of auto-fluorescence imaging in such a platform allows the clinician to assess the epithelium in the oral cavity for early markers of oral cancer. Auto-fluorescence imaging of the oral cavity for early markers of oral cancer include illumination with light in a first wavelength band and detection of light in a different auto-fluorescence wavelength band, as described in more detail below.

However, the real technical difficulty in comprehensive imaging of the oral cavity can be experienced simply by trying to take some images of the oral cavity using readily available commercial cameras, such as camera-phones like an IPHONE™ of APPLE INC.™ of Cupertino, Calif.

Inventors have developed a low cost oral cavity scanning tool based, in some embodiments, on widely available camera-phones. Two key technical innovations pioneered by the inventors make fast and comprehensive fluorescence imaging of the oral cavity possible using commercially available camera-phones in a matter of seconds. This ease of use with standardization of imaging angles (as is commonly used in X-ray imaging) opens the door for rapid diagnostics and classification of oral inflammations from malignant oral cancer. Advantageous aspects originate from geometrical optics applied to the specific problem of imaging the surface of the oral cavity.

In some embodiments, pinhole based camera-phone imaging is employed. The challenge of ultra-wide angle imaging of a spherical cavity can be met by an unconventional complete imaging technique known as pinhole imaging that does not rely on a material lens. Rather than using a focusing lens to project an image on a plane coincident with a sensor plane (e.g., a charge coupled device, CCD, array), a miniature pinhole is used to keep out-of-focus light from impinging on the sensor plane. This technique also eliminates the use of costly optical components that are difficult to mass-produce due to high manufacturing tolerance required for lenses made at small length scale. A small hole (with diameters in a range from about 1 micrometers, μm, to about 1000 μm, depending on ambient conditions, where 1 μm=$10^{-6}$ meters) can project light from the oral cavity directly onto a screen/wall/surface or be coupled to a camera/camera phone. For a pinhole imaging system, in some embodiments, a simple screen is used to form a real image and the camera phone or other camera takes an image of the screen (which is a real image) using native camera phone lenses and optics. In other embodiments, a direct capture method is used in which a bare CCD array is utilized (e.g., by removing the native lenses of a camera phone), which captures a direct image that forms on the bare CCD. Pinhole imaging provides an advantage of a very large field of view image that is in focus everywhere across the image.

In some embodiments, modular optical components, including a fish-eye lens in some embodiments, are used with optical transforms. To allow for 360 degree imaging of the oral cavity, the inventors have exploited the use of fish-eye lenses that snap onto any regular cellphone and thus provide a unique and complete coverage of the oral cavity. Since the geometrical transformation of the object and the image are both known, simple optical transforms in post-processing reverses the image to correct for optical aberration and provides a true area of lesions for diagnostic purposes.

Further, in some embodiments, the inventors have integrated an auto-fluorescence imaging scheme, with excitation wavelength of 488 nanometers (nm, 1 nm=$10^{-9}$ meters) provided by a blue light emitting diode (LED), and an optical filter deployed to block the excitation wavelength and other wavelengths, or pass just the fluorescence wavelengths between about 500 nm to about 600 nm (in the green range), depending on illness, and a cell phone camera acting as the imaging sensor.

Furthermore, in some embodiments, software tools are specifically written for post-processing, segmentation and labeling of these images to categorize collected samples in various bins based on several key morphological indicators in the given images. In various embodiments, a clustering approach is either trained to provide an autonomous diagnostic or is used as an aid for a trained specialist who finally labels the images as oral inflammations or suspected lesions likely to be oral cancer. In most cases, diseased tissue causes a region that is dimmer than the surrounding tissue. The exact percentage dimmer is determined in clinical trials. This threshold varies the clinical sensitivity of the device. In some embodiments, a dye (such as a Toluidine blue stain) is applied to the oral cavity of the subject before the image frame data is collected, to enhance the distinction between healthy and diseased tissue in the fluorescence frames.

It is anticipated that some embodiments will include a rapid screening platform, which allows for regular and large scale (hundreds of patients per worker per day) screening, and which is followed by traditional histological pathology based detection of cancer type in suspected cases. Rather than re-invent the wheel; it is anticipated further to use existing open-source mobile-programming platforms for healthcare delivery in the hardware and software tools, in various embodiments. This allows for an extremely critical, user-friendly and culturally acceptable graphical user interface (GUI). This also allows for rapid launch and test of the devices and methods described herein.

Plug-and-play modular optical components mounted on traditional camera-phones specifically target comprehensive and standardized imaging of the oral cavity. Pinhole based imaging is applied to camera-phones in some embodiments for ultra-low cost and robust imaging platforms. The GUI of such camera phones provide ease of use without prior training to make imaging the oral cavity as simple and intuitive as taking picture of a person's face. Standardization of imaging by mechanical constraints, applied using a simple mouthpiece on which the patient bites, automatically positions the imaging plane (camera) at a specific relative coordinate to the patients face.

This easy accessibility combined with convincing individuals of the great importance of oral hygiene in India (and similar low to middle income countries) presents itself as an opportunity to develop a health care delivery system based on a comprehensive, low-cost and fast imaging tool for the oral cavity.

Figure 2C:
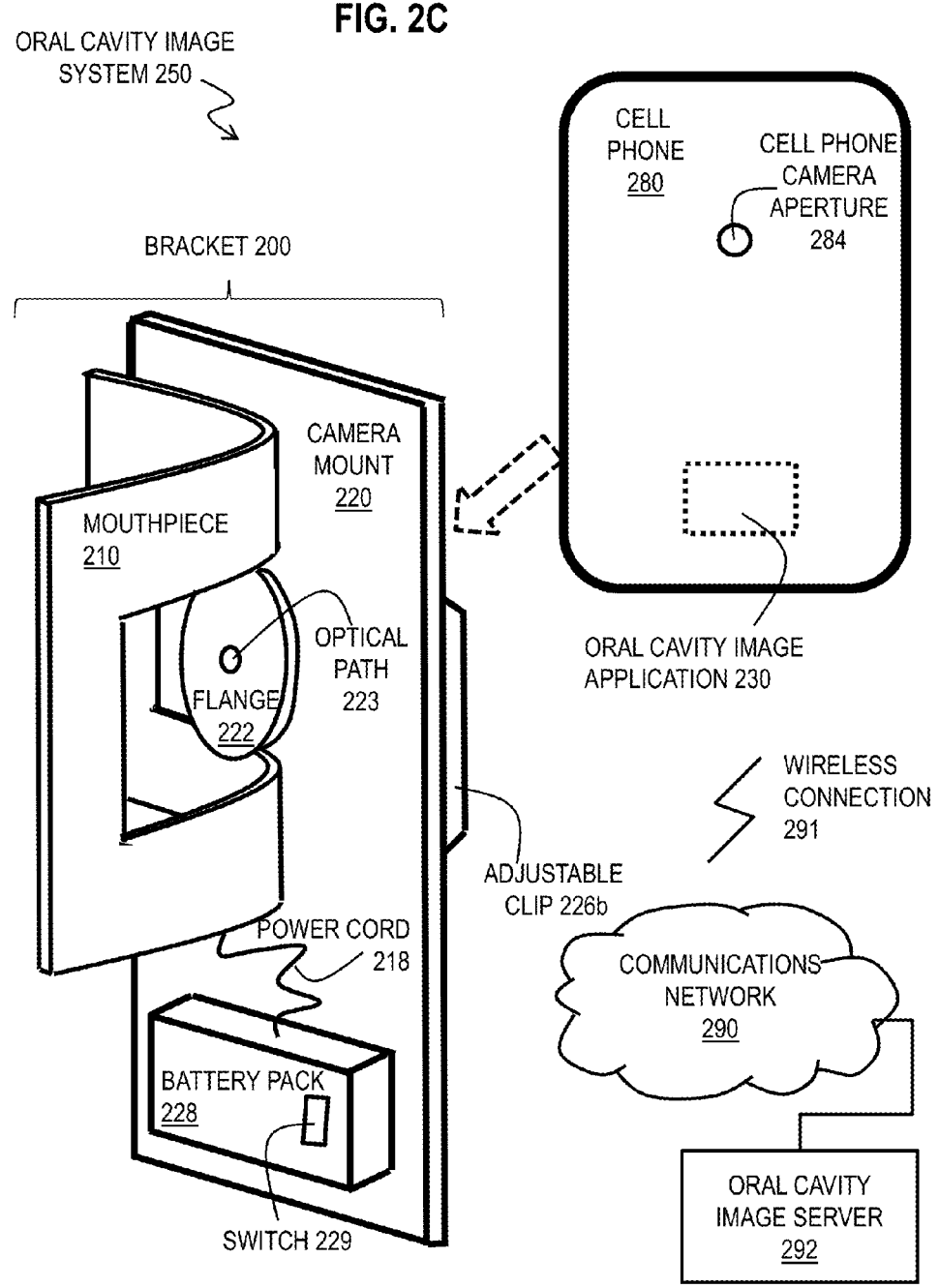

FIG. 2A, FIG. 2B and FIG. 2C are block diagrams that illustrate an example oral cavity image bracket 200 and system 250, according to an embodiment. In FIG. 2A a posterior view of the mouthpiece from a clinician's point of view is depicted. The posterior side of the bracket 200 is presented to a subject, such as a patient, to bite upon.

A mouthpiece 210 includes an upper bite guide 212a and a lower bite guide 212b, collectively referenced hereinafter as bite guides 212. The gums or teeth of the subject's upper jaw are placed inside the upper bite guide 212a. As depicted, the upper bite guide 212a comprises a flat area jutting out of the plane of the view of FIG. 2A far enough to accommodate the teeth or gums of a subject's upper jaw and at the outer edge turning upward to form the depicted trapezoidal shape. Similarly, the lower bite guide 212b comprises a flat area jutting out of the plane of the view of FIG. 2A far enough to accommodate the teeth or gums of a subject's lower jaw and at the outer edge turning downward to form the depicted trapezoidal shape. In various other embodiments, one or both of the bite guides 212 occupy a larger or smaller portion of the left to right dimension of the mouthpiece or involve a horizontal outward jutting portion with a groove configured to accommodate the gums or teeth of a subject, or some combination.

The mouthpiece 210 is made of a rigid material that does not substantively change shape when subjected to the pressures of the bite of a subject (e.g., changes shape less than about 20% and preferably less than about 1%). For example, in various embodiments the mouthpiece material is one or more of Nylon, Silicone, ABS plastic, Medical grade ABS plastic, polyurathane (mercury free), PMMA, PDMS, PET, Acrylic, Acetal Copolymet, Acetal Homopolymer, LCP, LDPE, LLDPE, Polycarbinate, PBT, PETG, polypropylene, thermoplastic elastomers, (basically any plastic or rubber that will not harm the human body), high density rigid foam, and medium density rigid foam. In various other embodiments, multiple materials are used in combination where one or more disposable parts are made from one kind of plastic (such as one listed above or otherwise) and the second portion is built from another plastic (such as one listed above or otherwise).

The bite guides are separated by an opening 211 that provides a view into the subject's oral cavity. As depicted, the opening 211 is closed at both left and right sides. However, in some embodiments the opening extends to the left side of the mouthpiece or to the right side of the mouthpiece. As depicted, the mouthpiece 210 is an integral piece of material; however, in some embodiments the left or right side of the opening 211 is a post made of a different material.

In various embodiments, the dimensions of the mouthpiece 210, bite guides 212, and opening 211 are configured to fit the mouths of patients of a certain size range, such as adults, adolescents, children or infants. For example, in some embodiments the mouthpiece dimensions are selected from a group of standard sizes, from about 1.5 centimeters to about 6 centimeters. The larger size the subject can withstand, the more of the subject's mouth can be imaged. Thus, the upper bite guide 212a and lower bite guide 212b are spaced apart such that a subject biting down on the upper bite guide 212a with the subject's upper jaw and biting up on the lower bite guide 212b with the subject's lower jaw opens the subject's oral cavity to inspection through the opening 211.

In the illustrated embodiment, the mouthpiece is curved out of the plane of the view of FIG. 2A to follow a typical shape of a face of a subject so that left side, right side and middle of the opening 211 in the mouthpiece are about equally far from the center of the surface of an oral cavity of a subject, where a back of the tongue of the subject normally leads to the top of the throat of the subject. In some embodiments, the mouthpiece is flat. Curving the mouthpiece offers the advantage of changing the angle of view of the imaging, so that regions of the buccal mucosa (inner part of cheek) that are near the lips can be seen. A scanner without a curved surface would miss this region.

In some embodiments, the posterior side of the mouthpiece 210 includes one or more sources of light in each of one or more light banks. In the illustrated embodiment, the mouthpiece includes four light banks 216a, 216b, 216c and 216d, collectively called light banks 216 hereinafter. In some embodiments, the light banks (e.g., light banks 216) include bright light sources with a wide wavelength band encompassing most or all of the visible spectrum. In some embodiments, one or more of the light banks 216 include a light source for exciting fluorescence emission from the tissue of the oral cavity of the subject, such as a blue LED at 488 nm wavelength to excite auto-fluorescence in human tissue of the oral cavity. Such auto-fluorescence indicates variations of health of the tissue within the oral cavity. In some embodiments, the mouthpiece includes a power source for the light banks 216 such as a battery pack. In the illustrated embodiment, the mouthpiece includes a power cord 218 that extends from the light banks 216 of the mouthpiece 210 to a power source, such as a battery pack, that resides off the mouthpiece 210.

In various embodiments, the mouthpiece 210 includes a space between the opening and the bite guides 212 and light banks 216 to allow a flange of a camera mount, described below, to slide along the opening. In some embodiments, the portion of the mouthpiece on the upper and lower edge of the opening, along which the flange slides, includes an upper rail 214a and lower rail 214b, respectively (collectively referenced hereinafter as rails 214) configured especially for this purpose. For example, in some embodiments, the rails 214 include a reinforced material, such as metal, or especially smooth coating, such as TEFLON™ produced by DUPONT CO.™ of Wilmington, Del., or other material, or some lubricant as may be well known in the art, or some combination. In embodiments using either nylon or ABS as the material of the mouthpiece 210, canola oil is advantageous as a lubricant because it is cheap and non-toxic. Some embodiments used thin metal as well as magnets (magnets were used in some embodiments to provide a continuously loaded bearing for smooth scanning, which especially helps with pushbroom imaging).

In some embodiments, a portion of the mouthpiece, such as a portion along the left or right side of the opening 211, is hinged to allow the flange 222 of the camera mount 220 to be inserted into the opening. In some embodiments, the rail is kept going throughout the device so that the flange just inserts into one of the sides.

The bracket 200 also includes a camera mount 220 that is configured to hold, on the opposite side (the anterior side facing the clinician) a camera to capture an image through the opening 211 in the mouthpiece 210. The posterior side of the camera mount 220, depicted in FIG. 2A, includes a flange 222 to engage the mouthpiece 210 along the opening 211, e.g., along rails 214, in such a way that the flange 222, and camera mount 220 of which the flange is part, can slide along the opening 211 of mouthpiece 210, as indicated by the dashed arrow in FIG. 2A. In some embodiments, the flange 222 is shaped so that when the camera mount 220 is rotated, as indicated by the curved arrow, the flange 222 disengages from the opening 211 of the mouthpiece 210; and, the camera mount 220 can be removed. The camera mount 220 can be engaged with the mouthpiece 210 by reversing this action. For example, when engaged, the flange 222 is larger in the vertical direction than the horizontal direction; e.g. the flange 222 is shaped as an oval with major axis aligned along the vertical when engaged with the opening 211, or shaped as a rectangle with the longer dimension aligned with the vertical when engaged with the opening 211.

The posterior side of the camera mount 220 includes an optical path 223 through to the anterior side of the camera mount at a position within the opening 211 so that light can pass from the oral cavity through the opening 211 and optical path 223 to the anterior side of the camera mount 220. Thus the optical path is configured for light to pass through the camera mount and through the opening in the mouthpiece. In some embodiments, the optical path is disposed beside the flange 222. In the illustrated embodiment, the optical path 223 passes through the flange 222.

In some embodiments, the optical path includes a pin hole that provides wide angle focus for all surfaces of the subject's oral cavity regardless of the varying distances from the pin hole to the surface of the subject's oral cavity. In some embodiments, a material lens, e.g., made of glass or plastic, is included in the optical path in addition to or instead of the pin hole. For example, in some embodiments, a fish eye lens, which expands the center of the field of view and compresses the edges, is included in the optical path.

In some embodiments, the optical path 223 includes a filter 225 that blocks light in a wavelength band corresponding to the fluorescence excitation light and passes light in a fluorescence emission wavelength band. In some embodiments, the filter 225 is configured to be moved into and out of the optical path 223. In such embodiments, the bracket 200 may be used to image both a bright light field (bright field) and a fluorescence emission field.

In some embodiments, the power source for the light banks 216 on the mouthpiece 210 is disposed on the camera mount 220. For example, as depicted, the power source is a battery pack 228 disposed on a posterior side of the camera mount 220; and, the power cord 218 for the light banks 216 on the mouthpiece 210 is connected to the battery pack 228.

FIG. 2B depicts the anterior view of the oral cavity image bracket 200. The mouthpiece 210, opening 211, rail 214a, rail 214b, camera mount 220 and optical path 223 are as described above for FIG. 2A.

The anterior side of the camera mount 220 includes one or more clips, such as adjustable clip 226a 226b and 226c (collectively referenced hereinafter as adjustable clips 226), for removably securing a camera to the anterior side of the camera mount 220. The adjustable clips 226 are disposed in tracks 227a, 227b, 227c, respectively, (collectively referenced hereinafter as tracks 227) so that the adjustable clips 226 can be moved along the tracks 227 to acquire a position useful for holding a camera in place so that the camera is positioned to capture an image through the optical path 223. In other embodiments, one or more clips are configured differently. For example, in some embodiments, the camera mount 220 is configured for a certain shaped camera, such as a camera cell phone, and the clips are not adjustable along a track, such as tracks 227. In some embodiments, each of one or more clips comprises a ledge extending out of the plane of FIG. 2B and a small plate perpendicular to the ledge at the outer edge of the ledge. Thus, the one or more clips are configured to removably hold a camera on the anterior side of the camera mount to record light passing through the optical path from the posterior side of the camera mount. In various embodiments, the clip is configured to removably hold a camera selected from a group comprising: a film camera; a digital camera; a digital camera with on board processor; a cell phone with digital camera; a programmable cell phone with digital camera, among others.

FIG. 2C depicts an example oral cavity image system 250, according to an embodiment. The illustrated system 250 includes the oral cavity image bracket 200, a cell phone 280 with digital camera, a communications network 290, and an oral cavity image server 292. In other embodiments, a digital camera is used instead of cell phone 280, or the communications network 290 and remote server 292 are omitted, or the system is changed in some combination of ways.

The oral cavity image bracket 200 is depicted in perspective and includes mouthpiece 210 and camera mount 220. The flange 222, optical path 223, adjustable clip 226b, power cord 218 and battery pack 228 are as described above. In the illustrated embodiment, the battery pack 228 includes a switch 229 configured to turn power on and off to the light banks 216 on mouthpiece 210.

The cell phone 280 includes a digital camera as is common in modern smart phones, such as mobile terminal 1301 described in more detail below with reference to FIG. 13. Light passing into the cell phone camera aperture 284 is captured by a sensor plane, such as a CCD array 1365 depicted in FIG. 13, and stored in the memory, e.g., memory 1351 depicted in FIG. 13, of the cell phone 280, e.g., mobile terminal 1300 of FIG. 13. The cell phone 280 includes an oral cavity image application 230 configured to execute on a microprocessor main control unit (MCU) of the cell phone 280, such as the MCU 1303 depicted in FIG. 13. The instructions for the oral cavity image application 230 are stored in memory 1351 until used by the MCU 1303.

Figure 13:
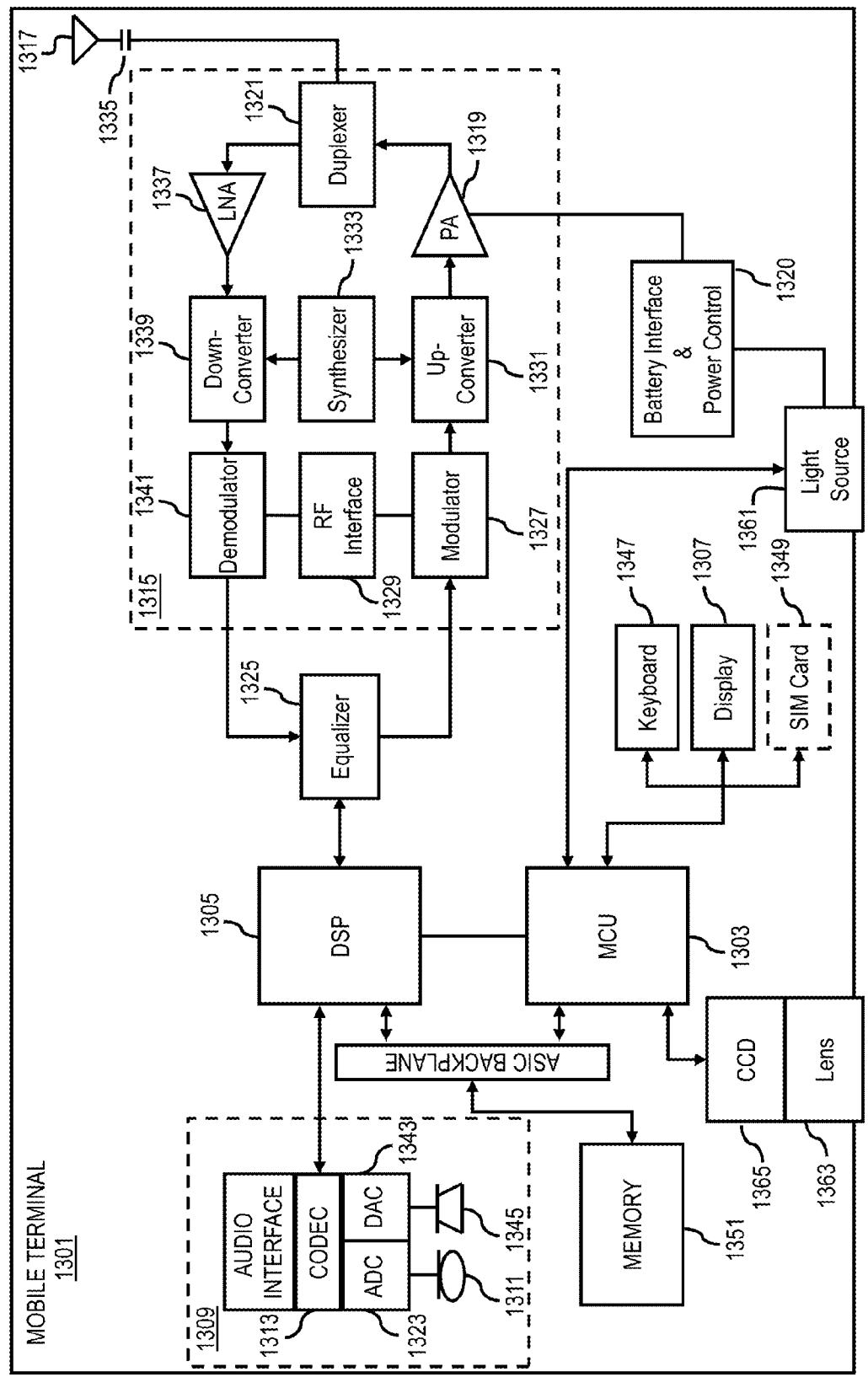
FIG. 13 is a block diagram that illustrates example components of a mobile terminal (e.g., a cell phone handset) for communications, which is capable of operating in the system of FIG. 2C, according to one embodiment.

The cell phone 280 also includes a transceiver, such as transceiver 1315 depicted in FIG. 13, for radio frequency communications with a communications network 290, such as a cell phone network, through wireless connection 291. In some embodiments, the oral cavity image application 230 is downloaded from an oral cavity image server 292 through the communications network 292 to the cell phone 280. In some embodiments, the oral cavity image application 230 performs all the processing to determine the standard image, for both bright field and fluorescence images, based on the light captured through the cell phone aperture 284. Both the captured images and the standardized image are displayed on the cell phone 280, e.g. on display 1307 depicted in FIG. 13. In some embodiments, some or all of the processing to determine the standard image based on the light captured through the cell phone aperture is performed by the remote oral cavity image server 292; and, image data is transmitted from the cell phone 280 to the server 292 through the communications network 290, and the resulting standardized image, whether a bright field or fluorescence image, is returned by the oral cavity image server 292 through the communications network 292 to the cell phone 280, where the standard image or images are displayed.

During operation of the system 250, the camera, such as cell phone 280, is a loaded onto the camera mount 220 as indicated by the dashed arrow in FIG. 2C. In some embodiments the adjustable clip 226b is replaced by a fixed shaped piece of rigid material, against which the cell phone may lodge.

Although processes, equipment, and data structures are depicted in FIG. 2C and following drawings as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, in some embodiments, a processor (not shown) is included on the oral cavity image bracket 200, such as on camera mount 220; and, the oral cavity image application 230 executes, in whole or in part, on the processor included on the oral cavity image bracket 200. In such embodiments, a wired (e.g., a universal serial bus, USB, cable) or wireless (e.g., Bluetooth) connection is established between the camera removably attached to the camera mount 220 and the processor on the bracket 200.

FIG. 3A, FIG. 3B and FIG. 3C are block diagrams that illustrate example fields of view from multiple positions of a camera mount 310 with cell phone attached along an opening in a mouthpiece 210 of the example oral cavity image bracket 200, according to an embodiment. Each of FIG. 3A, FIG. 3B and FIG. 3C shows operation of the bracket 200 from overhead looking down on the subject. A head 390 of the subject, such as a patient, is indicated with a mouthpiece 210 in place as the subject bites down on the bite guides 212. The oral cavity 392 of the subject is indicated by the dashed curve opening to the mouthpiece 210. The camera mount 310 with cell phone clipped in place is also depicted.

FIG. 3A depicts the camera mount 310 with cell phone in a first position farthest to the subject's left but still within the opening of the mouthpiece 210. The field of view 320a of the cell phone camera is depicted as a dotted triangle that captures light from the subject's right side and center of the subject's oral cavity 392. FIG. 3B depicts the camera mount 310 with cell phone in a second position within the middle of the opening of the mouthpiece 210. The field of view 320b of the cell phone camera is depicted as a dotted triangle that captures light from the center of the subject's oral cavity 392. FIG. 3C depicts the camera mount 310 with cell phone in a third position farthest to the subject's right but still within the opening of the mouthpiece 210. The field of view 320c of the cell phone camera is depicted as a dotted triangle that captures light from the subject's left side and center of the subject's oral cavity 392.

FIG. 3D is a block diagram that illustrates example overlapping raw image frames captured from the multiple positions of the camera mount, according to an embodiment. The projection of the target walls of the oral cavity 394 on the plane of the camera sensor is indicated by the dashed lines. The portion of that image captured by the cell phone camera in one position, e.g. the position of FIG. 3A, is shown as raw frame 330a. The portion of that image captured by the cell phone camera in another position, e.g. the position of FIG. 3B, is shown as raw frame 330b. The portion of that image captured by the cell phone camera in yet another position, e.g. the position of FIG. 3C, is shown as raw frame 330c. It is these multiple raw frames, such as frames 330a, 330b and 330c (collectively referenced hereinafter as raw frames 330), which are merged together to generate a standardized image by the oral cavity imaging processing method, such as oral cavity image application 230, and, optionally, oral cavity image server 292.

In some embodiments, the camera mount 220 is rotated several degrees in a plane perpendicular to the optical path while the flange 222 is still engaged with the mouthpiece 210 through the opening 211. In such embodiments, the raw frames include frames with a rotated view of the target walls of the oral cavity 394, compared to the views depicted in FIG. 3D; and, these raw frames are also included in the merge processing by the oral cavity image application 230 or oral cavity image server 192 or both. This can allow getting a wider field of view which can help get peripheral features (landscape mode). In portrait mode, it enables a broader amount of the hard palate and floor of the mouth (area under tongue).

Thus, in various embodiments, pioneering plug-and-play geometrical optics are deployed for use with camera-phones for medical applications; specifically targeted towards both bright field and fluorescence imaging of the oral cavity. The oral cavity presents a complex three dimensional surface making it extremely difficult to take images with comprehensive coverage that could be used as a standard for imaging the cavity. In fact, no prior standard (or platform) exists that can image the entire oral cavity. Embodiments of the present invention are anticipated to find great utility in field settings with shortage of doctors and oral surgeons, where clinicians often rely on memory to assess the extent of oral hygiene problems in patients of rural areas in many countries, e.g., because of excessive tobacco consumption.

2. Method

FIG. 4A is a flow chart that illustrates an example method 400 for producing and using one or more standard images of the oral cavity utilizing the oral cavity image bracket and a cell phone with built in camera and processor, according to an embodiment. Although steps are depicted in FIG. 4A, and in subsequent flowchart FIG. 4B, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

Figure 11:
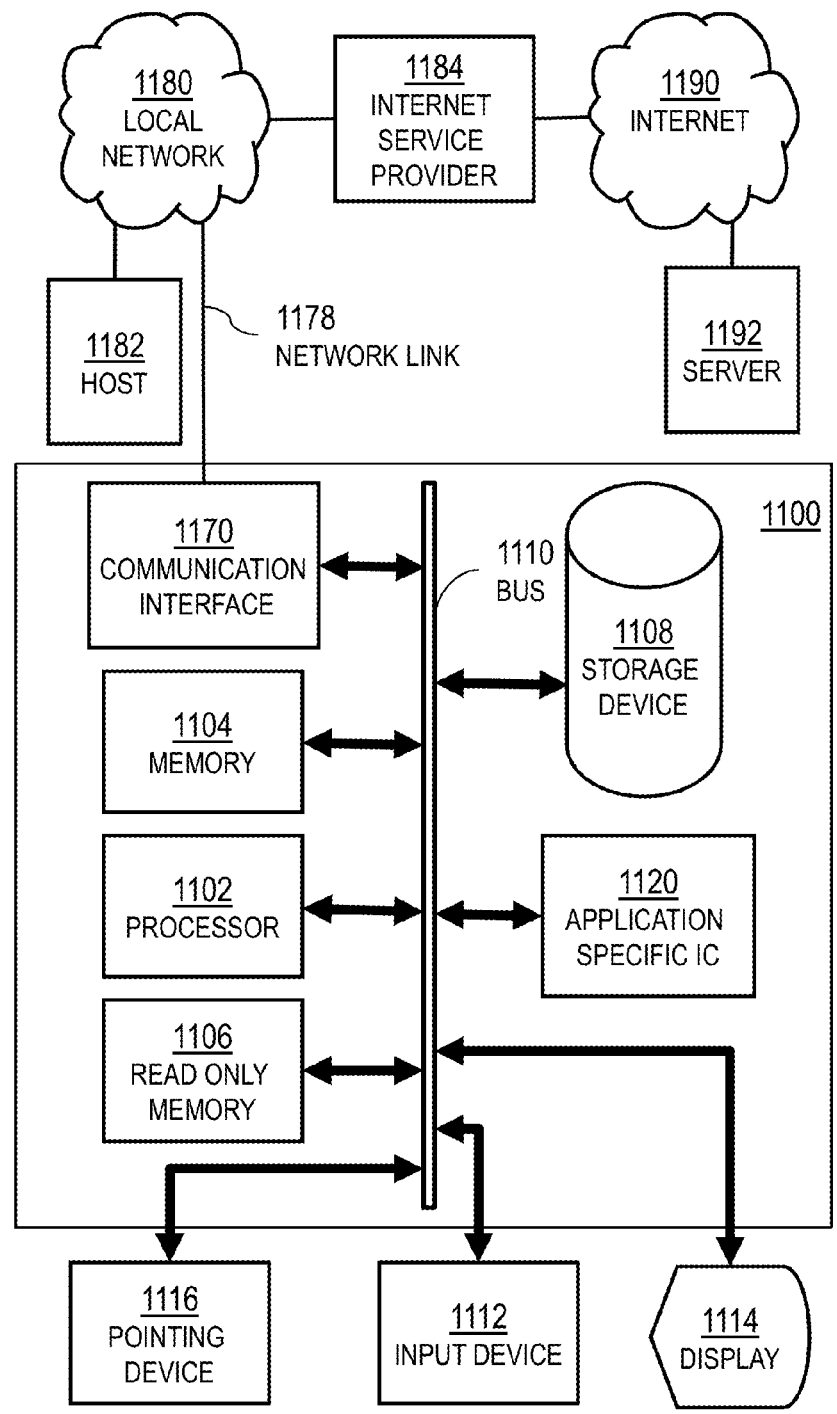
FIG. 11 is a block diagram that illustrates a computer system upon which an embodiment of the invention may be implemented.

In step 401, an oral cavity image application, such as oral cavity image application 230, is loaded into a cell phone equipped with digital camera, also known as a camera phone. Any method may be used to load the application into the camera phone, such as downloading the application from a remote server, such as the oral cavity image server 292. In some embodiments, the oral cavity image application 230 is loaded into the cell phone 280 through a cable connection to a computer, such as depicted in FIG. 11. In some embodiments, the oral cavity image application 230 is loaded into the cell phone 280 from a removable memory card, such as a SIM card 1349 depicted in FIG. 13. In some embodiments using a processor on the bracket 200 instead of the processor on the camera, step 401 includes loading the oral cavity image application 230 onto that processor on the bracket 200.

In step 403, the cell phone equipped with a camera and processor is removably attached to the camera mount of the oral cavity image bracket, e.g. using one or more clips on the camera mount such as one or more adjustable clips 236. The clips are configured to hold a camera, such as the cell phone 280, on the anterior side of the camera mount to record light passing through the optical path from the posterior side of the camera mount. In other embodiments, a different camera is mounted to the camera mount 220 in order to capture light transmitted through the optical path 223.

In step 405 the oral cavity image application 230 is executed, which prompts a user to enter patient and image metadata information into the application. In the illustrated embodiment, the application 230 executes on the cell phone 280 used as camera; and, the user interface of the cell phone 280 is used to prompt for and receive the metadata information. In other embodiments, a separate processor on the bracket 200 prompts for or receives the metadata or both through a separate interface, or using commands exchanged with the camera.

In step 407 the next subject (e.g., patient) is caused to bite down on the bite guides of the mouthpiece (e.g., on bite guides 214 of mouthpiece 210) to expose the subject's oral cavity to inspection through the opening (e.g., opening 211) in the mouthpiece (e.g., mouthpiece 210). In some embodiments, step 407 includes sanitizing the mouthpiece after use by one patient, or after prolonged non-use, for reuse with the next patient.

In step 409, it is determined whether fluorescence imaging is to be performed. In some embodiments this determination is made automatically. For example, a bright field image is automatically followed by a fluorescence image; or, every image is a bright field image; or, every image is a fluorescence image. In some embodiments, this determination is made by an operator.

If it is determined in step 409 that fluorescence imaging is not performed, then in step 411 the filter is positioned out of the optical path, either automatically or by manual operation by the operator/clinician. In some embodiments the filter, e.g., filter 225, is configured to pass only fluorescence emissions excited by light of wavelength near 488 nm. In step 412, the light banks of bright light are turned on. In some embodiments, as described in more detail below, the light banks 416 of bracket 200 are omitted, and the light of the camera, such as light source 1361 depicted in FIG. 13, of the cell phone is used as the bright field light source. Control then passes to step 417 described below.

If it is determined, in step 409, that a fluorescence image is to be performed, then in step 413 the filter is positioned in the optical path, again either automatically or by manual operation by the operator/clinician. In step 414, the fluorescence excitation light sources of the light banks 416 of bracket 200, e.g., blue LED lights, are turned on. In some embodiments, light banks 416 of bracket 200 are omitted; and, the light of the camera, such as light source 1361, of the cell phone is used as the light source. In some such embodiments, a second filter is placed over the light source of the cell phone to pass only the fluorescence excitation wavelengths, e.g., at 488 nm for auto-fluorescence. Control then passes to step 417.

In step 417, the camera mount 220 is slid along the opening 211 of the mouthpiece 210 to the first or next position for capturing a raw frame image of the subject's oral cavity. The camera, such as cell phone 280, is then operated to capture the raw frame image. The raw frame image is stored in the memory of the camera, such as the cell phone 280 (e.g., in memory 1351), or in a separate processor that is part of the bracket 200, or some combination.

In step 419, it is determined whether a raw image at another position is desired. If so, control passes back to step 417 to slide the camera mount to the next position along the opening of the mouthpiece and capture the next raw frame image using the camera, such as the cell phone 280. If no further raw images are desired in the current imaging mode (either bright field or fluorescence imaging), then control passes to step 421.

In step 421, it is determined whether another mode of imaging is desired. For example, it is determined whether a set of raw frame images in a bright field mode have been collected, but raw frame images in a fluorescence mode are still desired. If so, control passes back to step 409, described above. If not, control passes to step 423.

In step 423, the light banks are turned off and the oral cavity image application 230 is executed to merge several raw frame images into a standard image of the oral cavity of the subject. One or more standard images are produced, e.g., a bright field standard image and an auto-fluorescence standard image. In some embodiments, the standardized image is a set of standardized views with the subject's tongue in different positions. The process performed by the oral cavity image application 230 is described in more detail below with reference to FIG. 4B.

In step 425, the one or more standard images of the oral cavity of the subject are displayed for and analyzed by the operator/clinician. In addition, the raw frames or standard images or metadata or some combination is stored, either locally on the memory of the camera, such as memory 1351 of cell phone 280, or remotely on the oral cavity image server 192, or some combination. In some embodiments, step 425 includes recommendations by an automated algorithm on which areas of the image are suspect and worth a close examination by the clinician, or an estimated volume of a diseased areas, such as a lesion.

In step 427, it is determined whether there is another subject, such as another patient, to be examined using the oral cavity image system, such as system 250. If so, control passes back to step 405 described above. If not, the process 400 ends.

FIG. 4B is a flow chart that illustrates an example computer program method 440 for producing a standard image of the oral cavity based on overlapping image frames captured from the multiple positions of the camera mount, according to an embodiment. The method 440, in various embodiments, is performed by oral cavity image application 230 on the digital camera or camera phone or on a separate processor on the bracket 200, or by the remote oral cavity image server 292, or some combination. The method 440 uses two characteristic image manipulations: robust image mosaic formation; and, depth map based three dimensional (3-D) mesh generation for an individual oral cavity. Either one of the methods can be applied independently or in combination. The two methods can be applied for either a single image or multiple series of images.

In step 441, a prompt is sent to a display for the user to enter patient and image metadata, such as patient name, date and time, location, among others. Several screens of a graphical user interface (GUI) capable of such prompting are illustrated below with reference to FIG. 6A through FIG. 6C. In some embodiments, step 441 includes prompting the user and receiving input that indicates whether a pinhole or material lens is being used in the optical path. The former provides an in focus image for all portions of the surface of the oral cavity, while the latter focuses at a depth of field that can be used to infer the three-dimensional contours of the surface of the oral cavity, as described in more detail below. In some embodiments, step 441 includes prompting the user and receiving input that indicates whether fixed or dynamic lighting is to be used. In general, fixed lighting is attached to the mouthpiece, as depicted above as the light banks 216 in FIG. 2A; while, dynamic lighting is attached to the camera mount, e.g. camera mount 220 depicted in FIG. 2A. With dynamic lighting, the light intensity of a portion of the surface of the oral cavity is different for different frames captured by the camera on the camera mount.

In step 443, the next image frame is captured and received for the current patient and current mode. As used here "mode" refers to different lighting and optical characteristics of the capturing process, such as capturing a bright field image or an auto-fluorescence image. In some embodiments, step 443 includes detecting user selection of an active area on the GUI, such as a button labeled "take picture," that corresponds to capturing an image. The color and intensity measurements received at the optical sensor array are stored as image frame data, such as in a memory device in the camera, camera phone, or separate processor. In embodiments using a separate processor, image frame data captured at the camera is transmitted to the separate processor, either wirelessly or through a connected cable.

In step 445, it is determined whether the current image frame was taken with a material lens, such as through an optical path that includes a removable fish eye lens. If not, control passes to step 451, described below. If so, then control passes to step 447 to determine the distance of each pixel from the digital camera based on the focus. Any method known in the art to infer distance from focus and properties of the focusing lens may be used. In one embodiment, a depth map is constructed during step 447 using either single images or mosaic images utilizing algorithms described by Ashutosh Saxena, Sung H. Chung, Andrew Y. Ng, "Learning Depth from Single Monocular Images," in *Neural Information Processing Systems* (NIPS) v18, 2005, and Ashutosh Saxena, Min Sun, Andrew Y. Ng, "Make3D: Learning 3D Scene Structure from a Single Still Image," *IEEE Transactions of Pattern Analysis and Machine Intelligence* (PAMI), vol. 30, no. 5, pp 824-840, 2009, the entire contents of each of which are hereby incorporated by reference as if fully set forth herein, except for terminology that is incompatible with that used herein. In this embodiment, pixels that are in focus show a different net intensity than pixels out of focus. Given the characteristics of the lens, the distance to the pixels in focus can be determined.

As a result of this computation, the depths of the pixels in focus can be added to a 3-D model of the surface of the oral cavity and combined with other image frames, as described below, to produce a full 3-D mesh surface for the surface of the oral cavity. The advantage of applying this image processing method to oral cavity images comes from the fact that real geometrical quantities can be measured in metric units. Thus it is easy to quantify if a detected lesion is growing or shrinking. Consequently, automated marking and clustering of lesions based on size is possible. Control then passes to step 451.

In step 451, it is determined whether dynamic lighting is used during image frame capture, for example based on response to prompts in step 441. If not, control passes to step 461, described below. If so, control passes to step 453 to correct pixel intensity values on the frame based on the imaging geometry, such as the angle of illumination and the depth, if known, of the pixel. Control then passes to step 461.

In step 461, it is determined whether there is one or more previous image frames. In some embodiments, step 461 through step 473 are performed only after all frames have been captured for the current patient. In the illustrated embodiment, step 461 through step 473 are performed after each frame is captured. If there are no previous image frames, then control passes to step 471, described below. If there are one or more previous image frames, then control passes to step 463.

In step 463, the current image frame is registered with respect to the previous image frame using any registration method available known in the art. The step provides information that associates one or more pixels in a previous image frame with corresponding one or more pixels in the current image frame. In step 467, values for each pixel are determined based on the values in all corresponding pixels from any previous image frames. In one embodiment, the pixels are analyzed by column of pixels. For each pixel in the column, in this embodiment, the value is selected from a single pixel determined to be in focus, either because it was captured using a pinhole or was determined to be in focus during step 447, described above. In other embodiments, other procedures are used to combine the information from the corresponding pixels. For example, in some embodiments a median pixel value is selected; while, in other embodiments, a weighted or unweighted average of the corresponding pixels from two or more image frames is used as the pixel value. Control then passes to step 471. In an illustrated embodiment, the image mosaic is performed by algorithms using invariant features. See, for example, M. Brown and D. Lowe, "Automatic panoramic image stitching using invariant features," *International Journal of Computer Vision*, v74 no. 1, pp 59-73, 2007, the entire contents of which are hereby incorporated by reference as if fully set forth herein, except for terminology inconsistent with that used herein.

In step 471, it is determined whether the current image frame was captured in the fluorescence mode. If not, control passes to step 475, described below. If so, control passes to step 473. In step 473, pixels are classified as either normal or abnormal based on the relative intensity of the pixel values. Abnormal or diseased tissues fluoresce at a lower intensity than healthy tissue. Control then passes to step 475.

In step 475, it is determined whether there is another frame to be captured from the same patient. If so, control passes back to step 443, described above. If not, control passes to step 481. For example, the user selects an active area of the GUI to indicate completion of scanning the current patient, then control passes to step 481.

In Step 481, one or more standard images of the oral cavity in bright field or fluorescence mode, or both, are generated and displayed on the GUI, such as on the display of the cell phone. If a 3-D mesh has been computed, in some embodiments the 3-D mesh is optionally displayed over the image.

In step 483, the state of the tissue displayed in the one or more standard images is determined. For example based on the relative values within the image, or between the bright field and fluorescence images, or user input, or some combination, the healthy tissue is distinguished from the diseased tissue. In some embodiments that use the 3-D mesh, the volume of diseased tissue, such as the volume of a tumor, is determined during step 483.

In step 485, the one or more standard images and metadata, including any automated analysis results, are stored in memory, either on the local device or on the remote server 292. In step 487, it is determined whether there is another patient whose oral cavity is to be scanned. If so, control passes back to step 411. If not, then the process ends.

Thus, the method 440 uniquely combines mosaic based imaging (using one or more algorithms known to one of ordinary skill) and depth perception and 3D mesh generation from the same frames (using one or more different algorithms known to one of ordinary skill) for the special circumstances of oral screening. Collecting specified angular frames of known geometry and preparing the data for combining these two methods together allow a universal metric coordinate system that can be used to mark, measure and track lesions. Identification of lesions is done based on various threshold algorithms (using one or more still different algorithms known to one of ordinary skill) on this uniquely prepared data set.

3. Example Embodiments

Figure 5A:
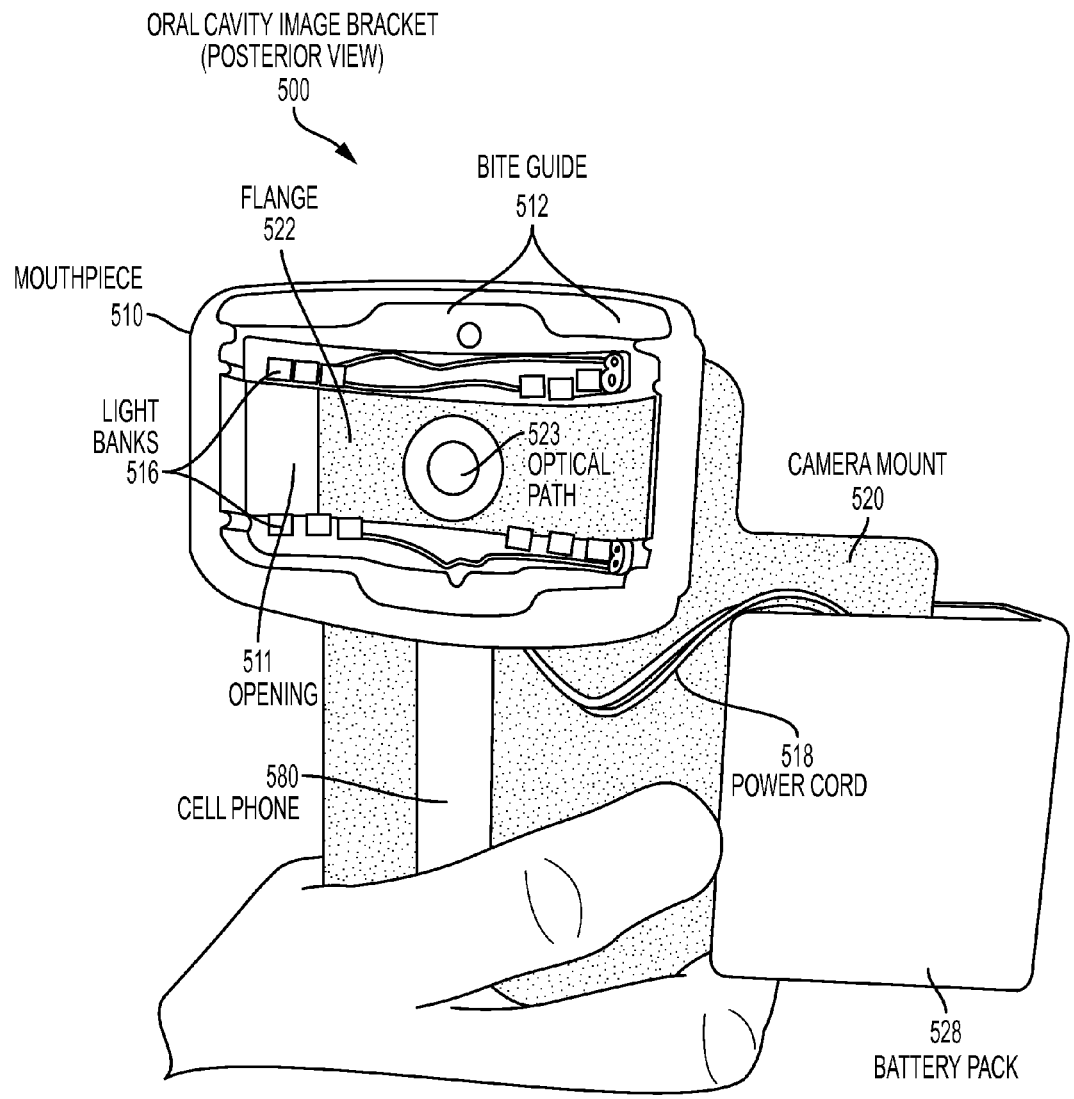
FIG. 5A and FIG. 5B are photographs that illustrate an example oral cavity image bracket and system, according to another embodiment.
Figure 5B:
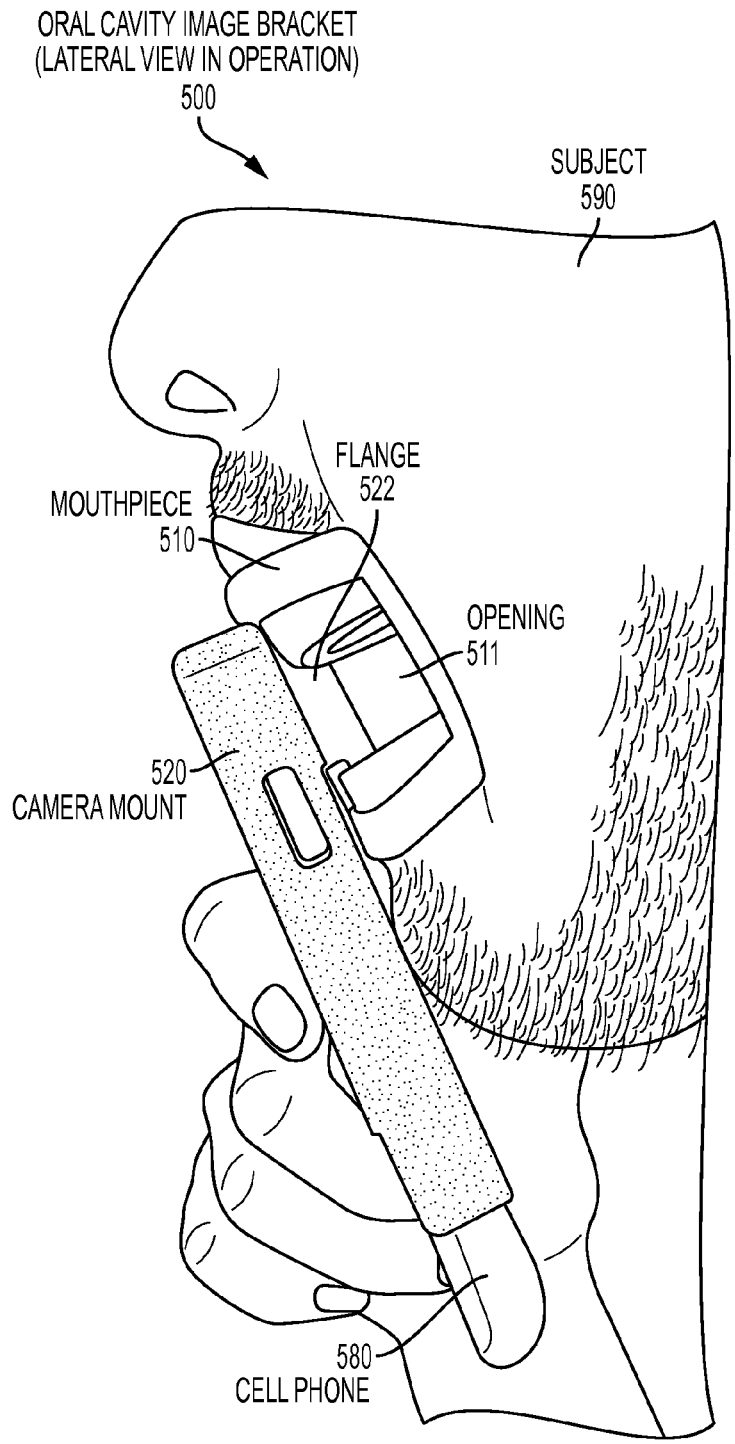

FIG. 5A and FIG. 5B are photographs that illustrate an example oral cavity image bracket and system, according to another embodiment. FIG. 5A is a photograph that depicts the posterior view of oral cavity image bracket 500 according to this embodiment. This embodiment includes mouthpiece 510 and camera mount 520. The mouthpiece 510 includes upper bite guide 512 that is made up of both a groove and a ledge with a plate turned up at the outer edge of the ledge. A similar lower bite plate is also shown. Between the upper and lower bite guides is mouthpiece opening 511. The mouthpiece 510 also includes light banks 516 that are illuminated and power cord 518 that connects to battery pack 528 on camera mount 520. The camera mount 520 includes flange 522 and optical path 523 as well as battery pack 528. Visible through an opening in the camera mount 520 is the dark body of cell phone 580 used to capture light that passes through optical path 523.

FIG. 5B is a photograph that depicts the oral cavity image bracket 500 in a lateral view during operation. Apparent in FIG. 5B is the mouthpiece 510 on which subject 590 is biting so as to present a view of the subject's oral cavity through opening 511. Also visible is the camera mount 520 engaged with the opening 511 of mouthpiece 510 by flange 522. Also visible is cell phone 580 removably attached to the camera mount 520, so that light passing through the optical path of camera mount 520 is captured by the camera aperture of cell phone 580. In some embodiments, portions of the camera mount 520 serves as a phone case. This type is manufactured differently for each type of phone. In some embodiments, the camera mount includes a flat substrate (such as a circuit board with a hole in it and lighting and battery attached, as described below with reference to FIG. 10D) that attaches via double sided office tape or double sided foam.

Figure 5C:
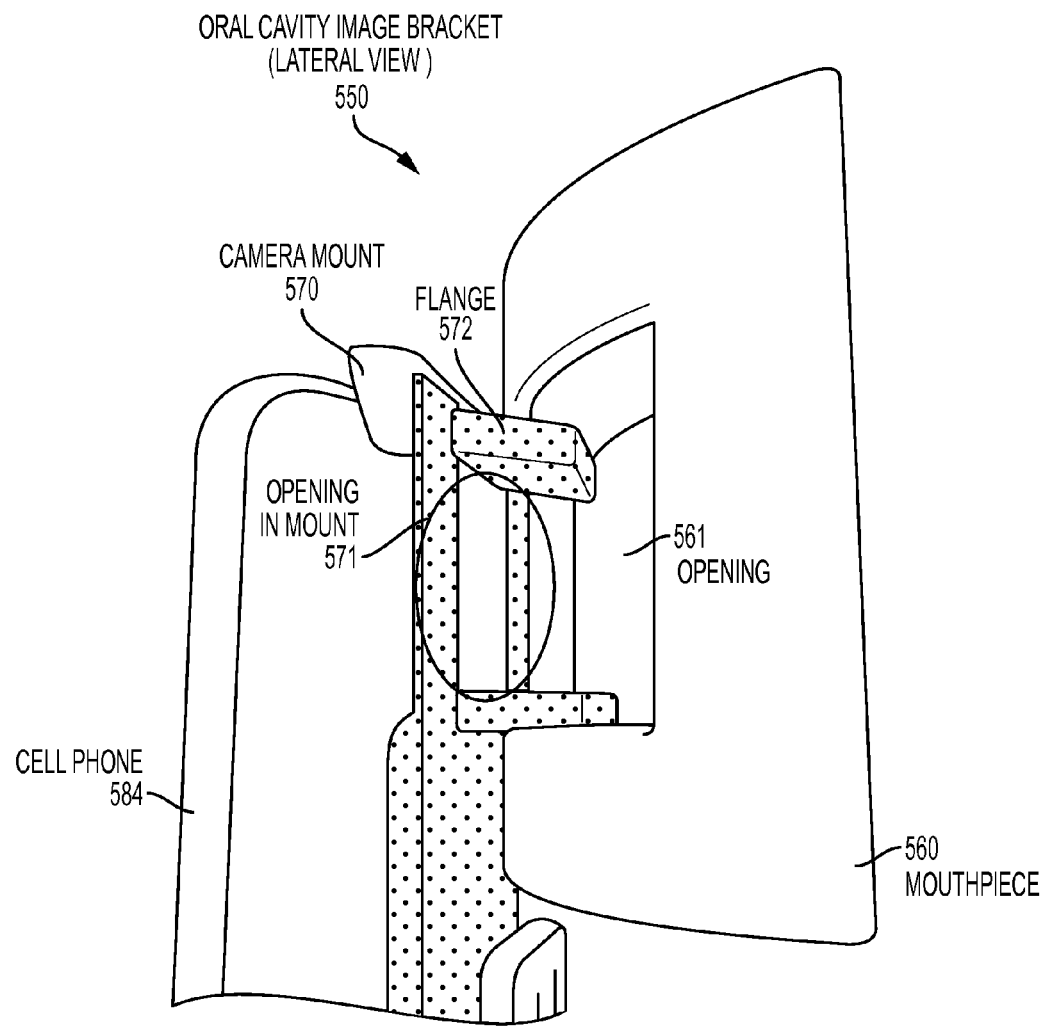
FIG. 5C and FIG. 5D are photographs that illustrate an example oral cavity image bracket and system, according to yet another embodiment.
Figure 5D:
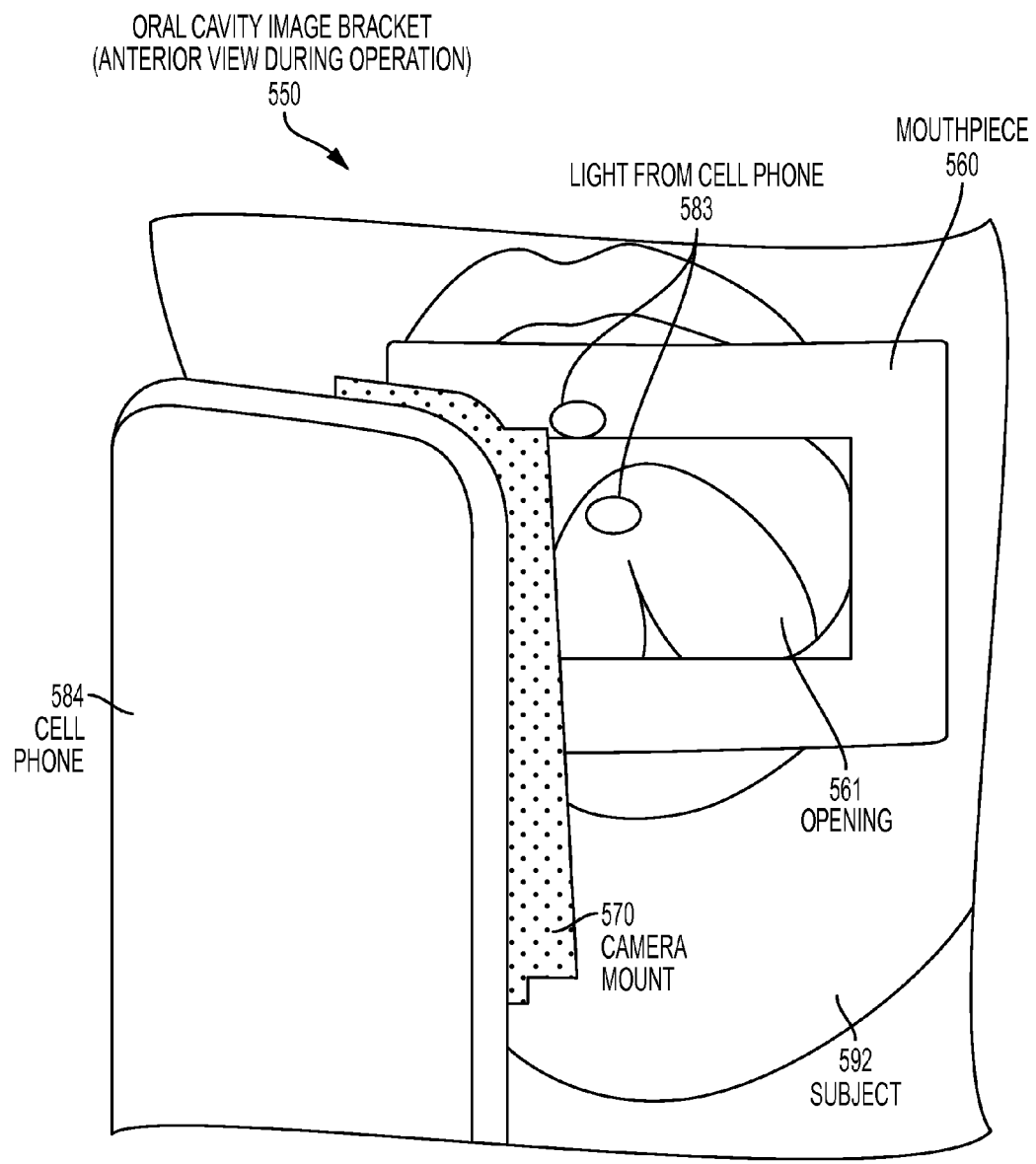

FIG. 5C and FIG. 5D are photographs that illustrate an example oral cavity image bracket 550 and system, according to yet another embodiment. FIG. 5C is a photograph that depicts a lateral view of oral cavity image bracket 550 according to this embodiment. This embodiment includes mouthpiece 560 and camera mount 570. The mouthpiece 560 includes mouthpiece opening 561. The mouthpiece 560 does not include light banks or a power cord or a battery pack. The camera mount 570 includes flange 572 and an opening 571 in the mount 570, which serves both as an optical path and a path for the light from a light source (e.g., light source 1361) of the camera (e.g., mobile terminal 1300) to illuminate the oral cavity. Also visible is the dark body of cell phone 584 used to capture light that passes through the opening 571 in the camera mount 570. This opening 571 in the camera mount 570 permits use of the cell phone camera aperture and cell phone light source in lieu of an optical path through the mount and light banks on the mouthpiece. In the illustrated embodiment, the flange 572 comprises two separate portions, an upper portion and a separate lower portion, and the opening 571 is disposed between the upper and lower portions of flange 572.

It is important to note the difference between the electronics setups in FIG. 5C and FIG. 5A. Some embodiments (e.g., FIG. 2A and FIG. 5A) utilize static lighting, wherein the illumination in the oral cavity does not change as the scan progresses. In the other embodiment (FIG. 5C) dynamic lighting occurs (the lighting moves as the scan progresses). Both modes have advantages and disadvantages. In static lighting, shadows stay put (which could make an area look suspicious in fluorescence). In dynamic lighting, it is possible to tell shadows from real suspicious regions; however, the intensity of lighting in a region changes in each image which can be problematic when tracking features FIG. 5D is a photograph that depicts the oral cavity image bracket 550 as an anterior view during operation. Apparent in FIG. 5D is the mouthpiece 560 on which subject 592 is biting so as to present a view of the subject's oral cavity through opening 561. Also visible is the camera mount 570 engaged with the opening 561 of mouthpiece 560 by flange 572. Also visible is cell phone 584 removably attached to the camera mount 570, so that light 583 from the cell phone light source illuminates the oral cavity of subject 592 and light passing through the optical path of camera mount 570 is captured by the camera aperture of cell phone 584.

Figure 6A:
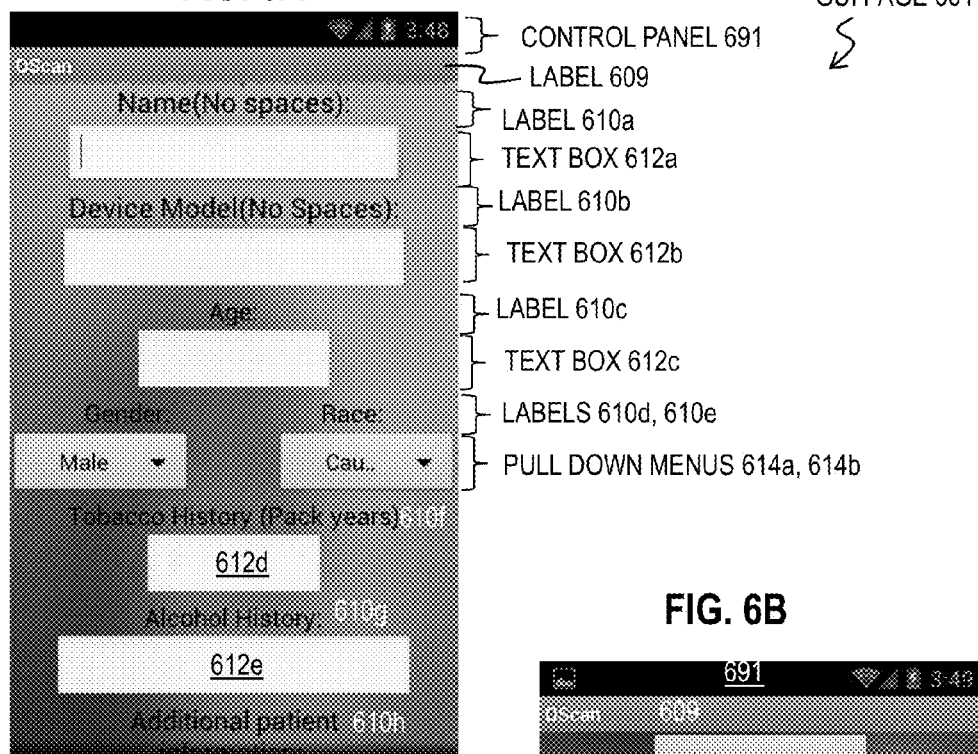
FIG. 6A through FIG. 6C are block diagrams that illustrate an example graphical user interface (GUI) for an oral cavity image application for a programmable cell phone with built-in camera and processor, according to another embodiment.
Figure 6B:
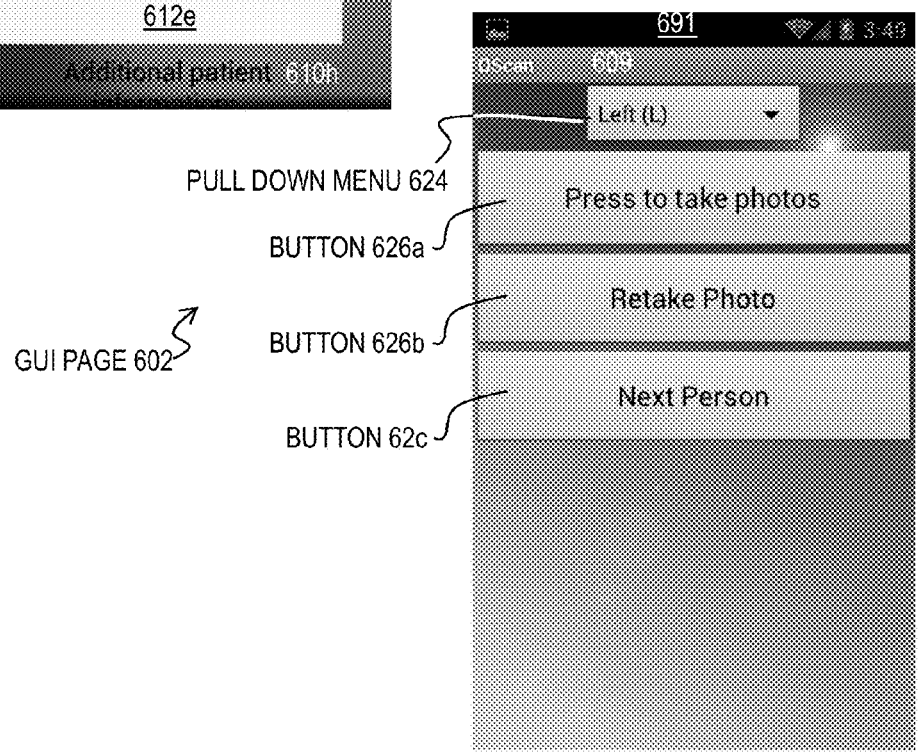
Figure 6C:
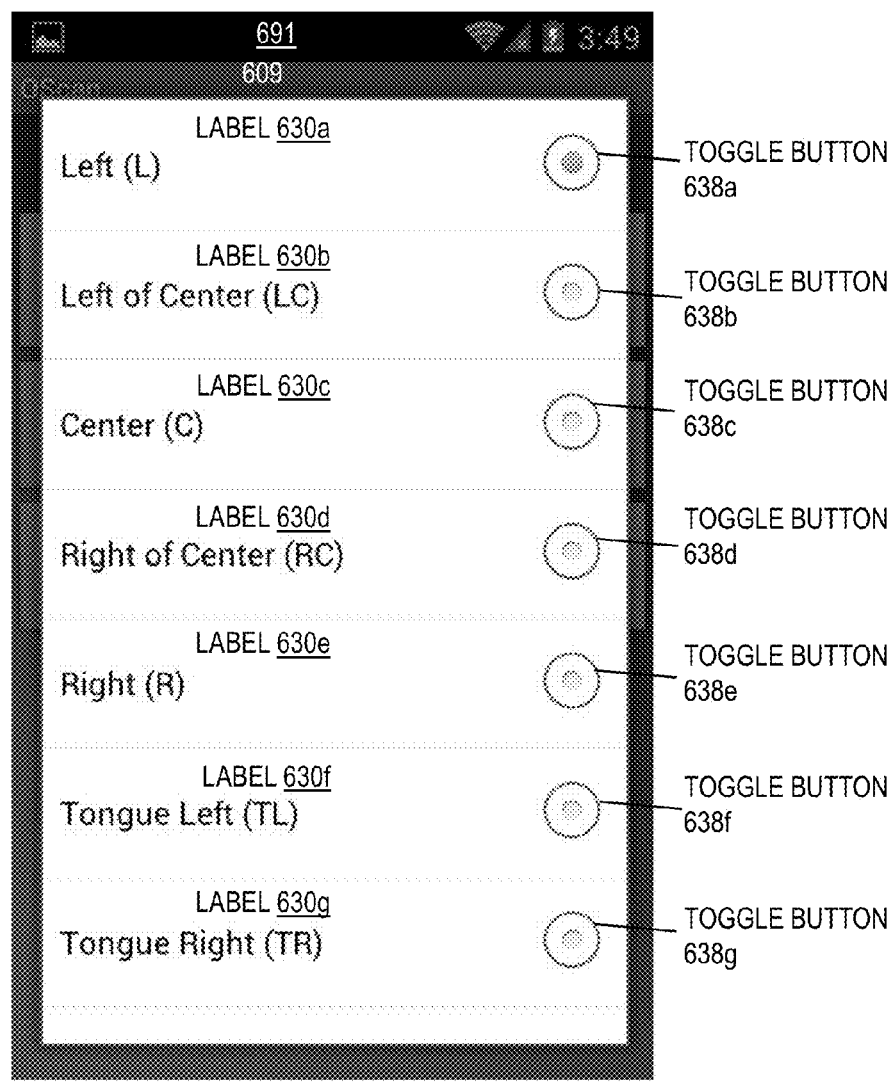
Figure 7:
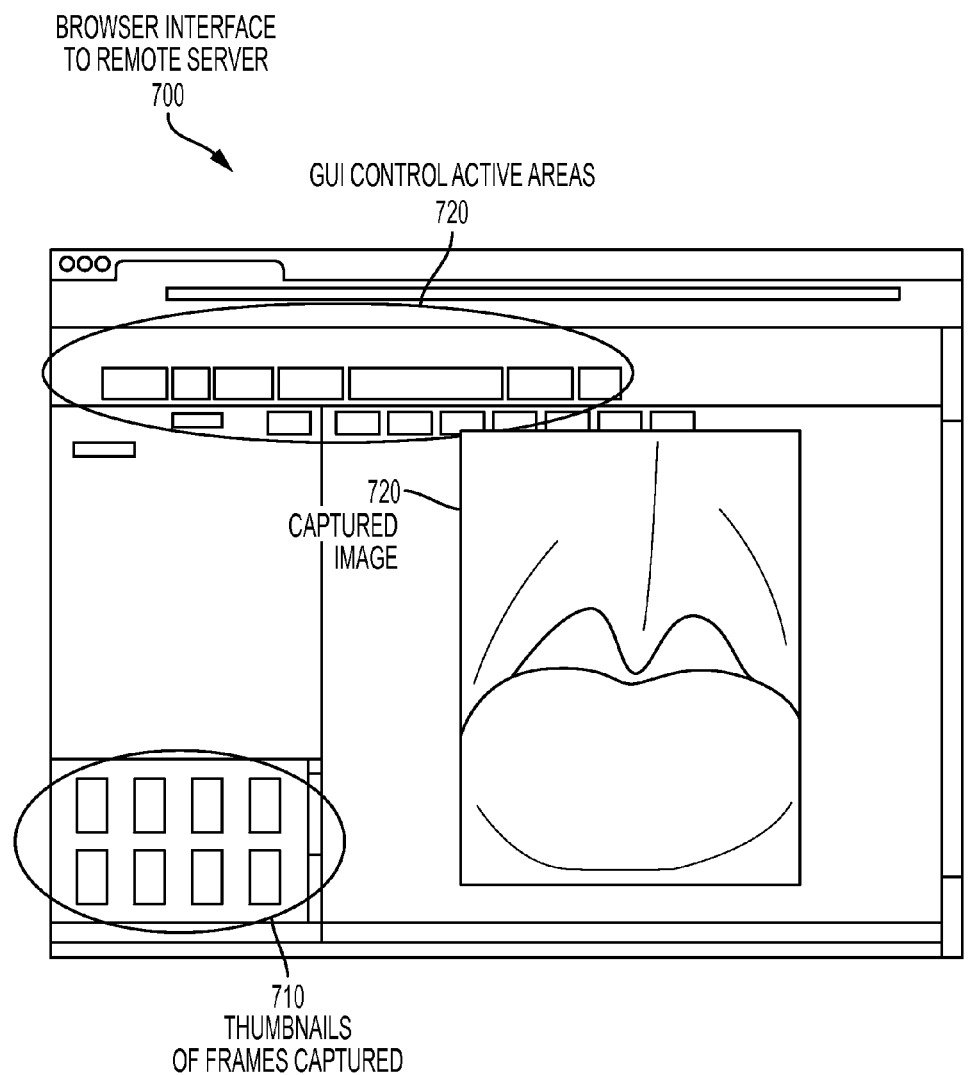
FIG. 7 is a block diagrams that illustrate an example browser graphical user interface (GUI) for a remote server configured for processing oral cavity images, according to another embodiment.

FIG. 6A through FIG. 7 are diagrams of user interfaces utilized in the processes of FIG. 4A, according to various embodiments. These figures illustrate an example graphical user interface for an oral cavity image application for a programmable cell phone with built-in camera and processor, according to another embodiment. The screen includes one or more active areas that allow a user to input data or operate the application. As is well known, an active area is a portion of a display to which a user can point using a pointing device (such as a cursor and cursor movement device, or a touch screen) to cause an action to be initiated by the device that includes the display. Well known forms of active areas are stand alone buttons, radio buttons, check lists, pull down menus, scrolling lists, and text boxes, among others. Although areas, active areas, windows and tool bars are depicted in FIG. 6A through FIG. 7 as integral blocks in a particular arrangement on particular screens for purposes of illustration, in other embodiments, one or more screens, windows or active areas, or portions thereof, are arranged in a different order, are of different types, or one or more are omitted, or additional areas are included or the user interfaces are changed in some combination of ways.

In FIG. 6A, the graphical user interface (GUI) of a display (e.g. 1307) of the cell phone (e.g. mobile terminal 1300) includes a first page 601 with a control panel 691 for operating the cell phone, and, specific to the oral cavity image application, e.g., application 230, a label 609 indicating the oral cavity scan application (Oscan in the illustrated embodiment). The page 601 also includes labels 610*a* through 610*h*, text boxes 612*a* through 612*e*, and pull down menus 614*a* and 164*b*. For example, label 610*a* includes the text "Please Enter Name (NO SPACES):" and text box 612*a* is configured to receive text entered by a user/clinician that indicates a name for the subject/patient. Similarly, label 610*b* includes the text "Device Model (NO SPACES):" and text box 612*b* is configured to receive text entered by a user/clinician that indicates the model of camera, digital camera or camera phone used to scan the oral cavity. Similarly, label 610*c* prompts for "Age" of the patient and text box 512*c* is configured to receive that information. Labels 610*d* and 610*e* prompt for "Gender" and "Race" of the patient and pull down menus 614*a* and 614 are configured to present a list of choices approved to receiving the data. Labels 610*f* and 610*g* prompt for "Tobacco history (Pack Years)" and "Alcohol History," while text boxes 612*d* and 612*e*, respectively, are configured to receive that data. A user can scroll down page 601 using normal controls for the device, such as sliding a finger along a touch screen display on the device. Text boxes off screen are scrolled to in order to receive other information that the user/clinician chooses to enter, such as the "Additional Patient information" prompted by label 610*h*.

The information provided by the user/clinician in the text boxes and pull down menus of page 601 constitutes metadata for the raw images to be captured and the standardized image to be generated. Patient background data is often just as important as the images collected. On other pages of the GUI, the user/clinician is prompted for additional information which, upon entry by the user/clinician, becomes metadata about the raw images captured and the standardized image produced. In some embodiments, an open source software tool (e.g., ANDROID™ based software tools from GOOGLE INC™ of Mountain View, Calif.) is used to allow for integrated GUI, metadata collection, and data management for a cell-phone based oral scanner.

In FIG. 6B, the graphical user interface (GUI) of a display (e.g. 1307) of the cell phone (e.g. mobile terminal 1300) includes another page 602 used for operating the OScan application, a particular embodiment of the oral cavity image application 230. Besides control panel 691 and application label 609, described above, page 602 includes pull down menu 624 and buttons 626*a* through 626*c*. The pull-down menu 624 lets the user/clinician indicate which frame is being captured among left, center, right, among others as listed in FIG. 6C, described below. Button 626*a*, labeled "Press to take photos," is configured to be activated by the user/clinician to cause the camera (e.g., mobile terminal 1300) to capture an image frame. Button 626*b*, labeled "Retake Photo," is configured to be activated by the user/clinician to cause the camera (e.g., mobile terminal 1300) to delete the last image frame and capture a new image frame. Button 626*c*, labeled "Next person," is configured to be activated by the user/clinician to cause the camera (e.g., mobile terminal 1300) to finish storing image frames and metadata for one subject so that such information can begin to be collected for another subject (e.g., to follow the YES branch from step 487 described in FIG. 4B, above.

In FIG. 6C, the graphical user interface (GUI) of a display (e.g. 1307) of the cell phone (e.g. mobile terminal 1300) includes yet another page 603 used for operating the OScan application. Besides control panel 691 and application label 609, described above, page 603 includes labels 630*a* through 630*g* and corresponding radio or toggle buttons 638*a* through 638*g*. The labels 630*a* through 630*g* indicate multiple locations for frames to capture, which are recommended for producing the standardized image. In the illustrated embodiment, seven locations indicated by the labels 630*a* through 630g are "Left (L)," "Left of Center (LC)," "Center (C)," "Right of Center (RC)," "Right (R)," "Tongue Left (TL)," "Tongue Right (TR)," respectively. The toggle buttons are filled, as depicted for toggle button 638a, as each frame at the corresponding location is captured and stored by the application on the camera, digital camera or camera phone, other equivalent device.

FIG. 7 is a block diagram that illustrates an example browser graphical user interface 700 for a remote server (e.g., remote oral cavity image server 292) configured for processing oral cavity images, according to another embodiment. As is well known in the art, a browser is a client process operating on a local device that interacts over a network with a server process using a particular communication protocol called the hypertext transfer protocol (HTTP) and a particular language to indicate formatting called the hypertext markup language (HTML). In the illustrated embodiment, browser interface 700 displays a captured raw image 720 (e.g., on display device 1114 of computer 1100 depicted in FIG. 11). The illustrated browser interface 700 also displays multiple thumbnails of frames captured 710 which are active areas the user/clinician can select to choose the raw image to display as captured raw image 720. Other GUI control active areas 720 are also presented in the browser interface 700 to allow the user/clinician to invoke various functions provided by the remote oral cavity image server 292. For example, in some embodiments, the GUI control active areas 720 include an active area to cause the remote oral cavity image server 292 to merge two or more of the raw images selected from the thumbnails of frames captured 710. In the illustrated embodiment, the captured raw frame image 720 and thumbnails of raw frames captured 710 are all bright field images in full color. In other embodiments, one or more captured raw frame image 720 and thumbnails of frames captured 710 are fluorescence raw frame images.

Figure 8:
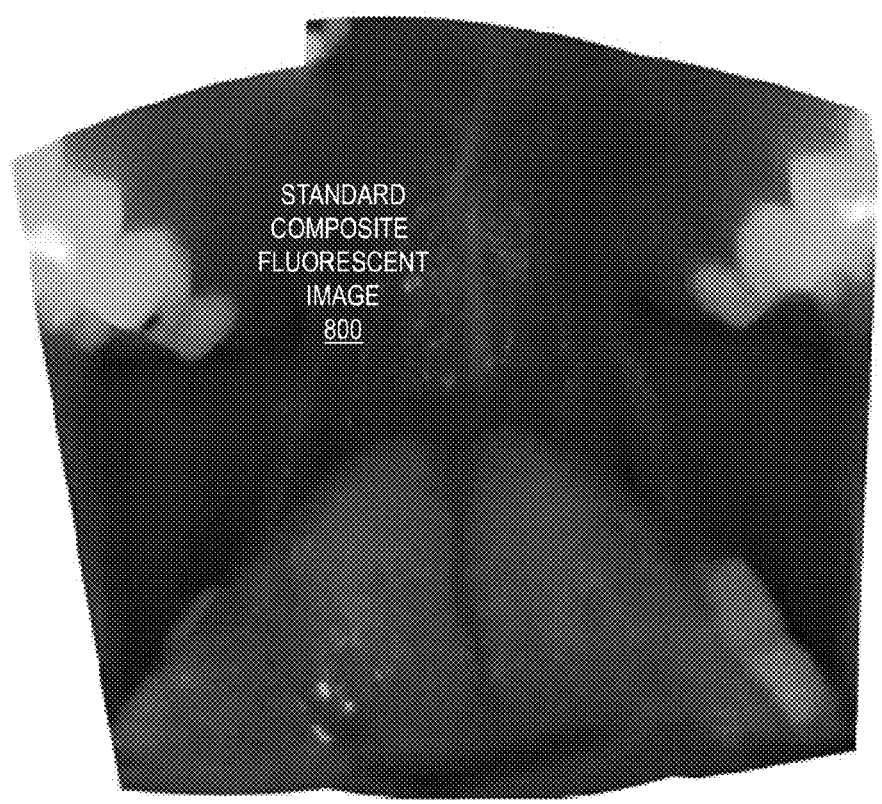
FIG. 8 is an image that illustrates an example standardized fluorescence image for an oral cavity, according to an embodiment.
Figures 9A, 9B, 9C, 9D, 9E, 9F:
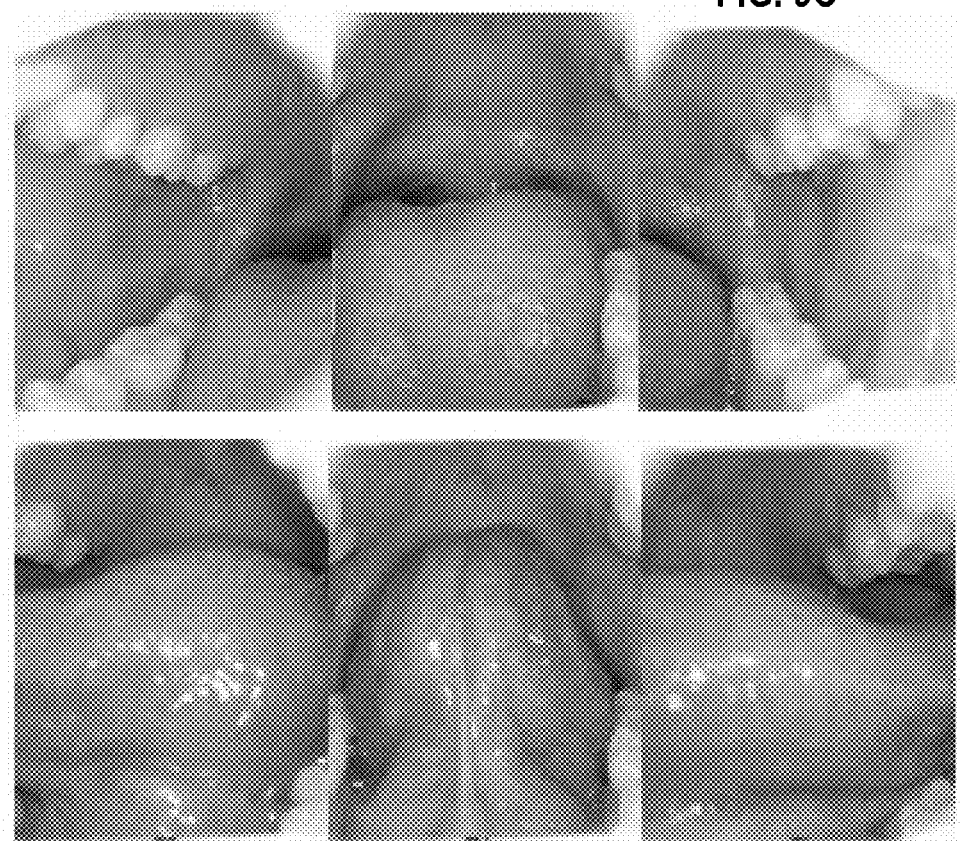
FIG. 9A through FIG. 9F are images that illustrate example bright field images for an oral cavity, according to an embodiment.

FIG. 8 is an image that illustrates an example standardized fluorescence image 800 for an oral cavity, according to an embodiment. The image 800 is a composite of multiple raw frame fluorescence images merged during step 423 of method 400, e.g. according to the method 440 of FIG. 4B. The image 800 is an image mosaic for comprehensive imaging of the oral cavity. The entire scan takes less than 1 minute to perform. As demonstrated by the above embodiment, a low-cost scanner for auto fluorescence imaging using a NEXSUS™ Phone from GOOGLE INC.™ as been implemented.

FIG. 9A through FIG. 9F are images that illustrate example bright field images for an oral cavity, according to an embodiment. These images are raw bright field images collected using a cellphone camera and its embedded optics only, without added fisheye lens or external pinhole. These are the standard positions that an oral specialist will place the tongue during an oral examination. These images are not merged, but the mosaic shows the high risk areas for cancer; and presents all of high risk areas for oral cancer in a single mosaic. Each standardized image may comprise one or more of these views after merging several raw frames.

Figure 10A:
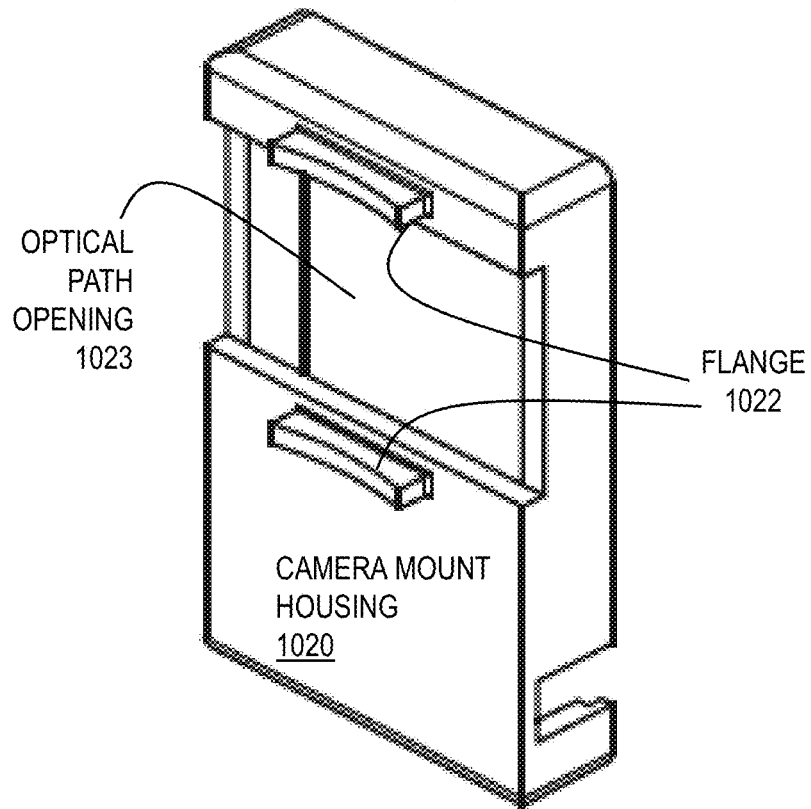
Figure 10B:
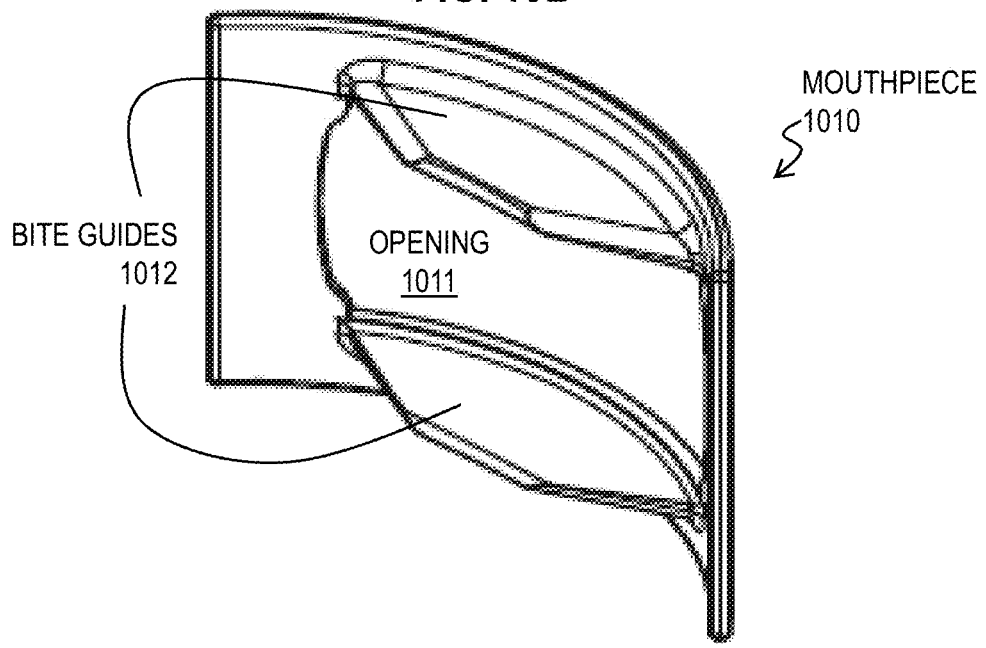

FIG. 10A through FIG. 10F are scaled drawings for a mouthpiece and camera mount, according to a particular embodiment. FIG. 10A depicts in oblique view a camera mount housing 1020 for a camera mount, such as camera mount 220. The housing 1020 includes a flange 1022 and optical path opening 1023. FIG. 10B depicts in a corresponding oblique view a mouthpiece 1010, such as 210. The mouthpiece 1010 includes opening 1011 and upper and lower bite guides 1012. FIG. 10F depicts mouthpiece 1010 in an opposite oblique view.

Figure 10C:
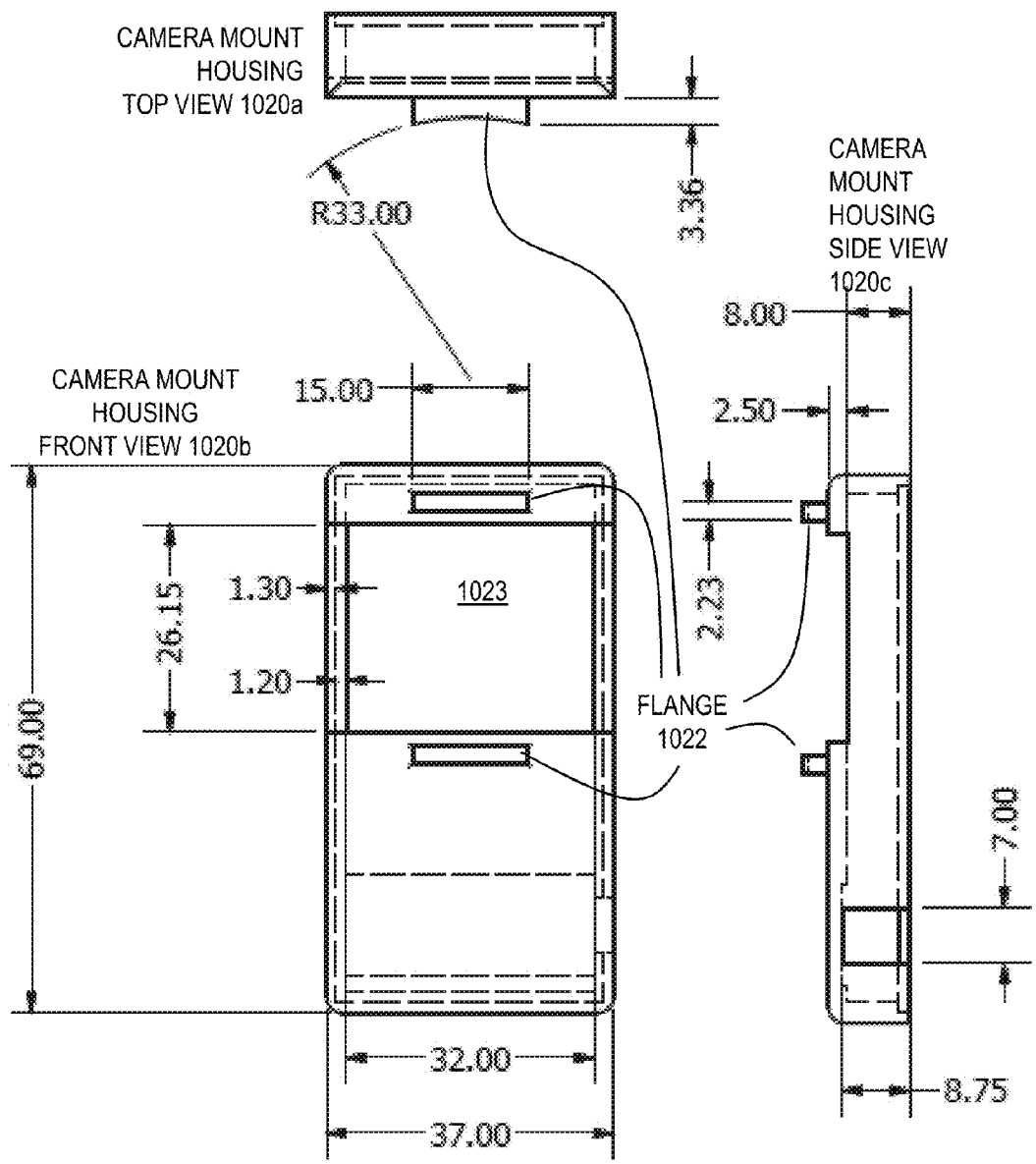

FIG. 10C depicts manufacturing drawings for the housing 1020, including aligned top view 1020a, front view 1020b, and side view 1020c, for a particular embodiment. In this embodiment, the distance associated with various dimensions are given in millimeters (mm, 1 mm=$10^{-3}$ meters). Thus, the housing width is about 37 mm, height is about 69 mm, opening 1023 is about 32 mm wide and 26.15 mm high. Each flange 1022 is about 15 mm wide, 2.23 mm high, and extends perpendicular to the face of the housing 1020 by up to 3.36 mm and curved with a radius of curvature of about 33 mm. the opening 1023 is set back from the face of the housing by about 2.5 mm, and the housing is about 8 mm thick. An opening in the side of the housing is about 8.75 mm from front to back and about 7 mm high.

Figure 10D:
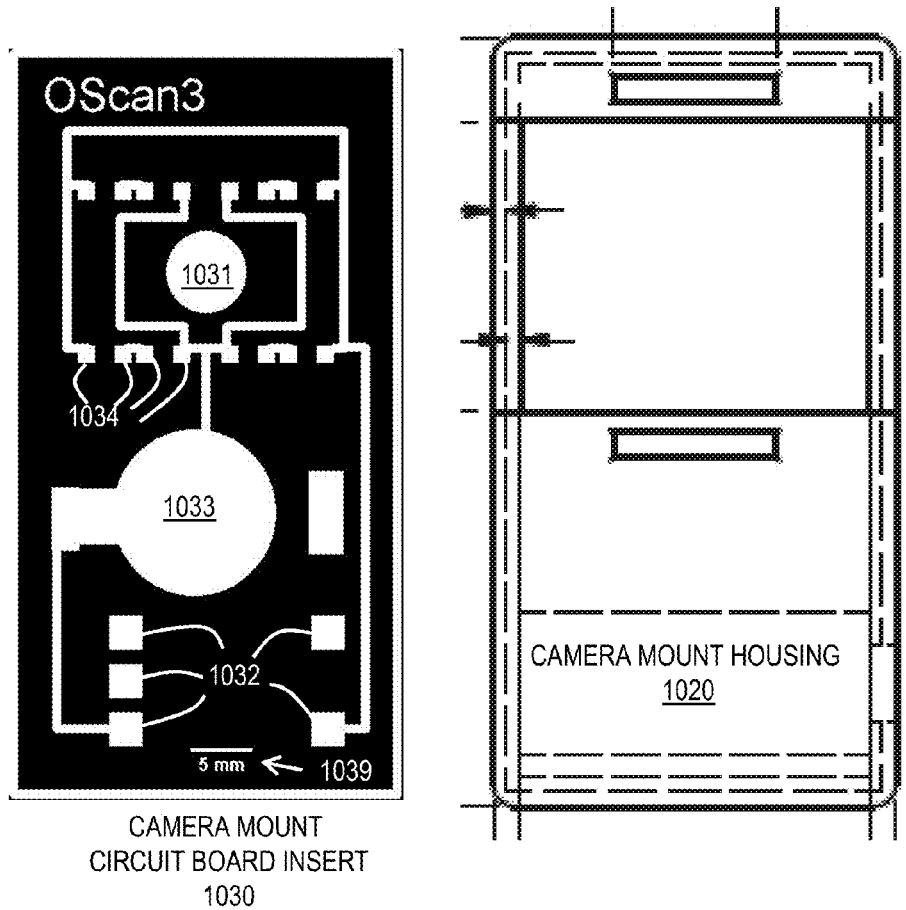

FIG. 10D depicts a camera mount circuit board insert 1030. This board is 29.9 mm wide and is press fit into the housing 1020 of the camera mount, shown alongside. The smaller hole 1031 of the two circular holes is a hole for the optical path. In some embodiments, a pin hole or fish eye lens is attached to this opening. The remaining white regions are where an electrical conductor, such as copper, is deposited. Dark regions are insulated. The 5 squares 1032 at the bottom of the image (near the scale bar 1039) accommodate a switch. The central circle 1033 and circuitry are for 2 stacked 3 Volt watch batteries, and the 16 squares (pads 1034) toward the top of the image are where the LEDs and resistors are soldered. After the holes are cut and the board 1030 is press fit into the housing 1020, the now combined housing and board is a camera mount that can be affixed to any camera or camera and lens system using double sided tape or double sided foam tape.

FIG. 10E depicts manufacturing drawings for the mouthpiece 1010, including an aligned top view 1010a, front view 1010b, and side view 1010c, for a particular embodiment. In this embodiment, the distance associated with various dimensions are given in millimeters. Thus, the mouthpiece width is about 60.17 mm, height is about 41.91 mm. Each bite guide 1012 is about 41.07 mm wide, about 1.65 mm high and separated by about 31.75 mm. The mouthpiece is curved with a radius of curvature of about 38.1 mm; and is about 1.59 mm thick. Opening 1011 is about 42.93 mm wide and about 25 mm high. The sides of the opening 1011 are curved with a radius of curvature of 50.42 mm.

4. Hardware Overview

FIG. 11 is a block diagram that illustrates a computer system 1100 upon which an embodiment of the invention may be implemented. Computer system 1100 includes a communication mechanism such as a bus 1110 for passing information between other internal and external components of the computer system 1100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit.).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1100, or a portion thereof, constitutes a means for performing one or more steps of one or more methods described herein.

A sequence of binary digits constitutes digital data that is used to represent a number or code for a character. A bus 1110 includes many parallel conductors of information so that information is transferred quickly among devices coupled to the bus 1110. One or more processors 1102 for processing information are coupled with the bus 1110. A processor 1102 performs a set of operations on information. The set of operations include bringing information in from the bus 1110 and placing information on the bus 1110. The set of operations also typically include comparing two or more units of information, shifting positions of units of information, and combining two or more units of information, such as by addition or multiplication. A sequence of operations to be executed by the processor 1102 constitute computer instructions.

Computer system 1100 also includes a memory 1104 coupled to bus 1110. The memory 1104, such as a random access memory (RAM) or other dynamic storage device, stores information including computer instructions. Dynamic memory allows information stored therein to be changed by the computer system 1100. RAM allows a unit of information stored at a location called a memory address to be stored and retrieved independently of information at neighboring addresses. The memory 1104 is also used by the processor 1102 to store temporary values during execution of computer instructions. The computer system 1100 also includes a read only memory (ROM) 1106 or other static storage device coupled to the bus 1110 for storing static information, including instructions, that is not changed by the computer system 1100. Also coupled to bus 1110 is a non-volatile (persistent) storage device 1108, such as a magnetic disk or optical disk, for storing information, including instructions, that persists even when the computer system 1100 is turned off or otherwise loses power.

Information, including instructions, is provided to the bus 1110 for use by the processor from an external input device 1112, such as a keyboard containing alphanumeric keys operated by a human user, or a sensor. A sensor detects conditions in its vicinity and transforms those detections into signals compatible with the signals used to represent information in computer system 1100. Other external devices coupled to bus 1110, used primarily for interacting with humans, include a display device 1114, such as a cathode ray tube (CRT) or a liquid crystal display (LCD), for presenting images, and a pointing device 1116, such as a mouse or a trackball or cursor direction keys, for controlling a position of a small cursor image presented on the display 1114 and issuing commands associated with graphical elements presented on the display 1114.

In the illustrated embodiment, special purpose hardware, such as an application specific integrated circuit (IC) 1120, is coupled to bus 1110. The special purpose hardware is configured to perform operations not performed by processor 1102 quickly enough for special purposes. Examples of application specific ICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1100 also includes one or more instances of a communications interface 1170 coupled to bus 1110. Communication interface 1170 provides a two-way communication coupling to a variety of external devices that operate with their own processors, such as printers, scanners and external disks. In general the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1170 sends and receives electrical, acoustic or electromagnetic signals, including infrared and optical signals, that carry information streams, such as digital data.

The term computer-readable medium is used herein to refer to any medium that participates in providing information to processor 1102, including instructions for execution. Such a medium may take many forms, including, but not limited to, non-volatile media, volatile media and transmission media. Non-volatile media include, for example, optical or magnetic disks, such as storage device 1108. Volatile media include, for example, dynamic memory 1104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1102, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1102, except for carrier waves and other signals.

Logic encoded in one or more tangible media includes one or both of processor instructions on a computer-readable storage media and special purpose hardware, such as ASIC 1120.

Network link 1178 typically provides information communication through one or more networks to other devices that use or process the information. For example, network link 1178 may provide a connection through local network 1180 to a host computer 1182 or to equipment 1184 operated by an Internet Service Provider (ISP). ISP equipment 1184 in turn provides data communication services through the public, world-wide packet-switching communication network of networks now commonly referred to as the Internet 1190. A computer called a server 1192 connected to the Internet provides a service in response to information received over the Internet. For example, server 1192 provides information representing video data for presentation at display 1114.

The invention is related to the use of computer system 1100 for implementing the techniques described herein. According to one embodiment of the invention, those techniques are performed by computer system 1100 in response to processor 1102 executing one or more sequences of one or more instructions contained in memory 1104. Such instructions, also called software and program code, may be read into memory 1104 from another computer-readable medium such as storage device 1108. Execution of the sequences of instructions contained in memory 1104 causes processor 1102 to perform the method steps described herein. In alternative embodiments, hardware, such as application specific integrated circuit 1120, may be used in place of or in combination with software to implement the invention. Thus, embodiments of the invention are not limited to any specific combination of hardware and software.

The signals transmitted over network link 1178 and other networks through communications interface 1170, carry information to and from computer system 1100. Computer system 1100 can send and receive information, including program code, through the networks 1180, 1190 among others, through network link 1178 and communications interface 1170. In an example using the Internet 1190, a server 1192 transmits program code for a particular application, requested by a message sent from computer 1100, through Internet 1190, ISP equipment 1184, local network 1180 and communications interface 1170. The received code may be executed by processor 1102 as it is received, or may be stored in storage device 1108 or other non-volatile storage for later execution, or both. In this manner, computer system 1100 may obtain application program code in the form of a signal on a carrier wave.

Various forms of computer readable media may be involved in carrying one or more sequence of instructions or data or both to processor 1102 for execution. For example, instructions and data may initially be carried on a magnetic disk of a remote computer such as host 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red a carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1102 retrieves and executes the instructions using some of the data sent with the instructions. The instructions and data received in memory 1104 may optionally be stored on storage device 1108, either before or after execution by the processor 1102.

Figure 12:
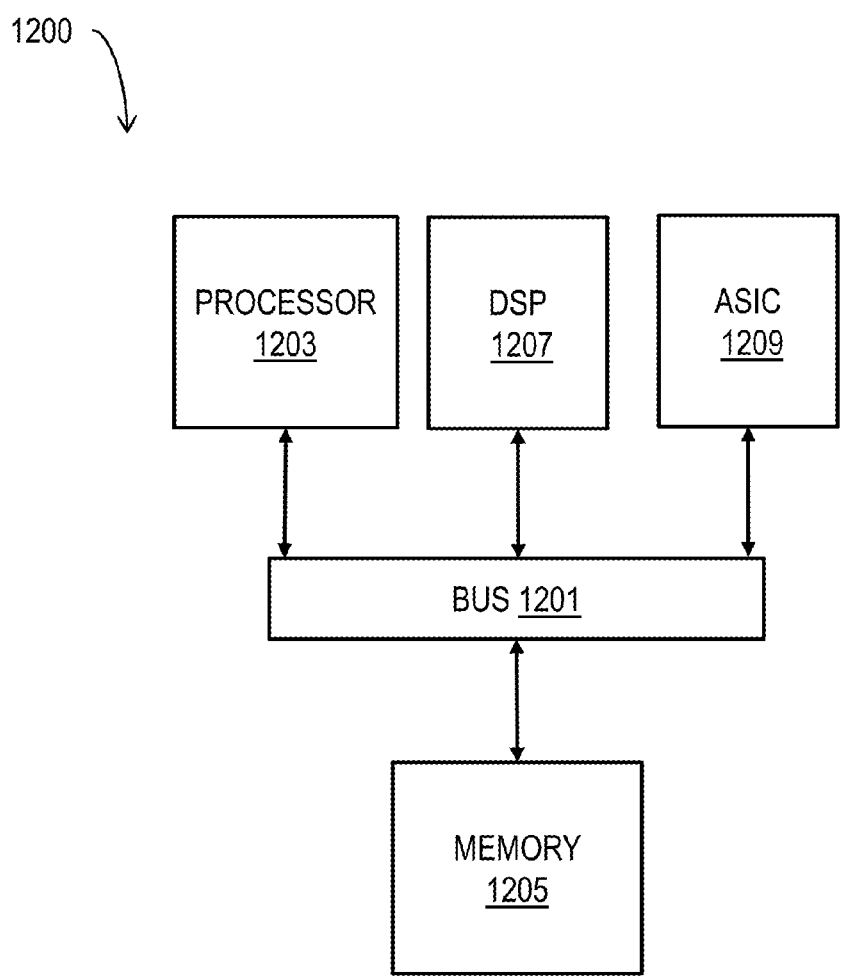
FIG. 12 illustrates a chip set upon which an embodiment of the invention may be implemented.

FIG. 12 illustrates a chip set 1200 upon which an embodiment of the invention may be implemented. Chip set 1200 is programmed to perform one or more steps of a method described herein and includes, for instance, the processor and memory components described with respect to FIG. 11 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1200, or a portion thereof, constitutes a means for performing one or more steps of a method described herein.

In one embodiment, the chip set 1200 includes a communication mechanism such as a bus 1201 for passing information among the components of the chip set 1200. A processor 1203 has connectivity to the bus 1201 to execute instructions and process information stored in, for example, a memory 1205. The processor 1203 may include one or more processing cores with each core configured to perform independently. A multi-core processor enables multiprocessing within a single physical package. Examples of a multi-core processor include two, four, eight, or greater numbers of processing cores. Alternatively or in addition, the processor 1203 may include one or more microprocessors configured in tandem via the bus 1201 to enable independent execution of instructions, pipelining, and multithreading. The processor 1203 may also be accompanied with one or more specialized components to perform certain processing functions and tasks such as one or more digital signal processors (DSP) 1207, or one or more application-specific integrated circuits (ASIC) 1209. A DSP 1207 typically is configured to process real-world signals (e.g., sound) in real time independently of the processor 1203. Similarly, an ASIC 1209 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1203 and accompanying components have connectivity to the memory 1205 via the bus 1201. The memory 1205 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1205 also stores the data associated with or generated by the execution of one or more steps of the methods described herein.

FIG. 13 is a diagram of exemplary components of a mobile terminal 1300 (e.g., cell phone handset) for communications, which is capable of operating in the system of FIG. 2C, according to one embodiment. In some embodiments, mobile terminal 1301, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1303, a Digital Signal Processor (DSP) 1305, and a receiver/transmitter unit including a microphone gain control unit and a speaker gain control unit. A main display unit 1307 provides a display to the user in support of various applications and mobile terminal functions that perform or support the steps as described herein. The display 1307 includes display circuitry configured to display at least a portion of a user interface of the mobile terminal (e.g., mobile telephone). Additionally, the display 1307 and display circuitry are configured to facilitate user control of at least some functions of the mobile terminal. An audio function circuitry 1309 includes a microphone 1311 and microphone amplifier that amplifies the speech signal output from the microphone 1311. The amplified speech signal output from the microphone 1311 is fed to a coder/decoder (CODEC) 1313.

A radio section 1315 amplifies power and converts frequency in order to communicate with a base station, which is included in a mobile communication system, via antenna 1317. The power amplifier (PA) 1319 and the transmitter/modulation circuitry are operationally responsive to the MCU 1303, with an output from the PA 1319 coupled to the duplexer 1321 or circulator or antenna switch, as known in the art. The PA 1319 also couples to a battery interface and power control unit 1320.

In use, a user of mobile terminal 1301 speaks into the microphone 1311 and his or her voice along with any detected background noise is converted into an analog voltage. The analog voltage is then converted into a digital signal through the Analog to Digital Converter (ADC) 1323. The control unit 1303 routes the digital signal into the DSP 1305 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1325 for compensation of any frequency-dependent impairments that occur during transmission though the air such as phase and amplitude distortion. After equalizing the bit stream, the modulator 1327 combines the signal with a RF signal generated in the RF interface 1329. The modulator 1327 generates a sine wave by way of frequency or phase modulation. In order to prepare the signal for transmission, an up-converter 1331 combines the sine wave output from the modulator 1327 with another sine wave generated by a synthesizer 1333 to achieve the desired frequency of transmission. The signal is then sent through a PA 1319 to increase the signal to an appropriate power level. In practical systems, the PA 1319 acts as a variable gain amplifier whose gain is controlled by the DSP 1305 from information received from a network base station. The signal is then filtered within the duplexer 1321 and optionally sent to an antenna coupler 1335 to match impedances to provide maximum power transfer. Finally, the signal is transmitted via antenna 1317 to a local base station. An automatic gain control (AGC) can be supplied to control the gain of the final stages of the receiver. The signals may be forwarded from there to a remote telephone which may be another cellular telephone, any other mobile phone or a landline connected to a Public Switched Telephone Network (PSTN), or other telephony networks.

Voice signals transmitted to the mobile terminal 1301 are received via antenna 1317 and immediately amplified by a low noise amplifier (LNA) 1337. A down-converter 1339 lowers the carrier frequency while the demodulator 1341 strips away the RF leaving only a digital bit stream. The signal then goes through the equalizer 1325 and is processed by the DSP 1305. A Digital to Analog Converter (DAC) 1343 converts the signal and the resulting output is transmitted to the user through the speaker 1345, all under control of a Main Control Unit (MCU) 1303 which can be implemented as a Central Processing Unit (CPU) (not shown).

The MCU 1303 receives various signals including input signals from the keyboard 1347. The keyboard 1347 and/or the MCU 1303 in combination with other user input components (e.g., the microphone 1311) comprise a user interface circuitry for managing user input. The MCU 1303 runs a user interface software to facilitate user control of at least some functions of the mobile terminal 1301 as described herein. The MCU 1303 also delivers a display command and a switch command to the display 1307 and to the speech output switching controller, respectively. Further, the MCU 1303 exchanges information with the DSP 1305 and can access an optionally incorporated SIM card 1349 and a memory 1351. In addition, the MCU 1303 executes various control functions required of the terminal. The DSP 1305 may, depending upon the implementation, perform any of a variety of conventional digital processing functions on the voice signals. Additionally, DSP 1305 determines the background noise level of the local environment from the signals detected by microphone 1311 and sets the gain of microphone 1311 to a level selected to compensate for the natural tendency of the user of the mobile terminal 1301.

The CODEC 1313 includes the ADC 1323 and DAC 1343. The memory 1351 stores various data including call incoming tone data and is capable of storing other data including music data received via, e.g., the global Internet. The software module could reside in RAM memory, flash memory, registers, or any other form of writable storage medium known in the art. The memory device 1351 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1349 carries, for instance, important information, such as the cellular phone number, the carrier supplying service, subscription details, and security information. The SIM card 1349 serves primarily to identify the mobile terminal 1301 on a radio network. The card 1349 also contains a memory for storing a personal telephone number registry, text messages, and user specific mobile terminal settings.

In some embodiments, the mobile terminal 1301 includes a digital camera comprising an array of optical detectors, such as charge coupled device (CCD) array 1365. The output of the array is image data that is transferred to the MCU for further processing or storage in the memory 1351 or both. In the illustrated embodiment, the light impinges on the optical array through a lens 1363, such as a pin-hole lens or a material lens made of an optical grade glass or plastic material. In the illustrated embodiment, the mobile terminal 1301 includes a light source 1361, such as a LED to illuminate a subject for capture by the optical array, e.g., CCD 1365. The light source is powered by the battery interface and power control module 1320 and controlled by the MCU 1303 based on instructions stored or loaded into the MCU 1303.

5. Extensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

What is claimed is:

1. An oral cavity image bracket comprising:
    a mouthpiece of rigid material comprising an upper bite guide and a lower bite guide, both disposed on a posterior side of the mouthpiece and separated by an opening through the mouthpiece, wherein the upper bite guide and lower bite guide are spaced apart such that a subject biting down on the upper bite guide with the subject's upper jaw and biting up on the lower bite guide with the subject's lower jaw opens the subject's oral cavity to inspection through the opening; and
    a camera mount disposed on an anterior side of the mouthpiece and comprising a flange configured to engage and slide along the opening of the mouthpiece,
    wherein the camera mount further comprises
        an optical path configured for light to pass through the camera mount and through the opening in the mouthpiece, and
        a clip disposed on an anterior side of the camera mount, wherein the clip is configured to removeably hold a camera on the anterior side of the camera mount to record light passing through the optical path from the posterior side of the camera mount.

2. An oral cavity image bracket as recited in claim 1, wherein the clip is configured to removeably hold a camera selected from a group comprising: a digital camera; a digital camera with on board processor; a cell phone with digital camera; a programmable cell phone with digital camera.

3. An oral cavity image bracket as recited in claim 1, wherein the optical path comprises a pin hole lens.

4. An oral cavity image bracket as recited in claim 1, wherein the optical path comprises a material lens.

5. An oral cavity image bracket as recited in claim 1, wherein the optical path comprises a removeable optical filter that blocks light from a light source and passes fluorescent light emitted by tissue in the oral cavity of the subject in response to the light source.

6. An oral cavity image bracket as recited in claim 1, wherein the mouthpiece further comprises a light source disposed on the posterior side of the mouthpiece and configured to illuminate the oral cavity of the subject.

7. An oral cavity image bracket as recited in claim 6, wherein at least one of the mouthpiece or the camera mount comprises a power source configured to supply power to the light source.

8. An oral cavity image system comprising:
    a bracket comprising
        a mouthpiece of rigid material comprising an upper bite guide and a lower bite guide, both disposed on a posterior side of the mouthpiece and separated by an opening through the mouthpiece, wherein the upper bite guide and lower bite guide are spaced apart such that a subject biting down on the upper bite guide with the subject's upper jaw and biting up on the lower bite guide with the subject's lower jaw opens the subject's oral cavity to inspection through the opening; and
        a camera mount disposed on an anterior side of the mouthpiece and comprising a flange configured to engage and slide along the opening of the mouthpiece, wherein the camera mount further comprises an optical path for light to pass through the camera mount and through the opening in the mouthpiece;
    a camera removeably attached to the anterior side of the camera mount, wherein the camera is configured to record and display an image based on light passing through the optical path from the posterior side of the camera mount; and
    a processor configured to merge data from a plurality of images recorded by the camera at a corresponding plurality of positions of the camera mount as the camera mount slides along the opening in the mouthpiece.

9. An oral cavity image system as recited in claim 8, wherein the posterior side of the mouthpiece further comprises a light source configured to illuminate the oral cavity of the subject.

10. An oral cavity image system as recited in claim 8, wherein the camera is selected from a group comprising: a digital camera; a digital camera with the processor on board; a cell phone with digital camera; a programmable cell phone with digital camera and with the processor on board.

11. An oral cavity image system as recited in claim 8, wherein the camera further comprises a light source configured to illuminate the oral cavity of the subject.

12. An oral cavity image system as recited in claim 8, wherein
    the system further comprises a communications module configured to communicate with a remote server; and
    the processor includes a processor on the remote server.

13. An oral cavity image system as recited in claim 8, wherein the camera is further configured to display an image based on the data merged by the processor from a plurality of images recorded by the camera.

14. A method comprising:
    removeably attaching a camera to a camera mount of a bracket comprising the camera mount and a mouthpiece, wherein
        the mouthpiece comprises an upper bite guide and a lower bite guide, both disposed on a posterior side of the mouthpiece and separated by an opening through the mouthpiece, wherein the upper bite guide and lower bite guide are spaced apart such that a subject biting down on the upper bite guide with the subject's upper jaw and biting up on the lower bite guide with the subject's lower jaw opens the subject's oral cavity to inspection through the opening,
        the camera mount is disposed on an anterior side of the mouthpiece and comprises a flange configured to engage and slide along the opening of the mouthpiece and an optical path for light to pass through the camera mount and through the opening in the mouthpiece, and the camera is configured to record and display an image based on light passing through the optical path from the posterior side of the camera mount;

causing a subject to bite against the bite guides of the mouthpiece;

sliding the camera mount to a plurality of positions along the opening in the mouthpiece; and causing the camera to capture a plurality of images corresponding to the plurality of positions.

15. A method as recited in claim 14, further comprising using a processor to merge data from the plurality of images into a standard image.

16. A method as recited in claim 15, further comprising displaying the standard image.

17. A method as recited in claim 16, further comprising viewing the standard image and determining a condition of subject based on the standard image.

18. A method as recited in claim 14, further comprising inserting a filter into the optical path, wherein the filter blocks light from a light source that illuminates the subject's oral cavity and passes light fluorescently emitted by tissue in the subject's oral cavity.

19. A method as recited in claim 14, further comprising activating a light source to illuminate the subject's oral cavity.

20. A method as recited in claim 14, wherein the light source is disposed on an posterior surface of the mouthpiece.

21. A method as recited in claim 14, wherein the camera is a programmable cell phone with camera and on-board processor.

\* \* \* \* \*